(12) United States Patent

Fernandez-Moure et al.

(10) Patent No.: US 12,690,889 B2

(45) Date of Patent: Jul. 28, 2026

(54) DEVICE AND METHOD FOR ACCESSING A CAVITY

(71) Applicant: Duke University, Durham, NC (US)

(72) Inventors: Joseph S. Fernandez-Moure, Durham, NC (US); Jacob Peloquin, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 292 days.

(21) Appl. No.: 18/318,822

(22) Filed: May 17, 2023

(65) Prior Publication Data

US 2023/0371983 A1 Nov. 23, 2023

Related U.S. Application Data

(60) Provisional application No. 63/342,672, filed on May 17, 2022.

(51) Int. Cl.
*A61B 17/34* (2006.01)
(52) U.S. Cl.
CPC ...... *A61B 17/3496* (2013.01); *A61B 17/3421* (2013.01); *A61B 2017/346* (2013.01)
(58) Field of Classification Search
CPC ............ A61B 17/3496; A61B 17/3421; A61B 2017/346; A61B 1/05; A61B 1/313; A61B 17/34; A61B 90/03; A61B 90/30; A61B 2017/00907; A61B 2017/3427; A61B 2017/3454; A61B 2017/347; A61B 2017/349; A61B 2090/0811; A61B 17/3417; A61B 17/3423; A61B 2017/3425; A61B 2017/3433; A61B 17/3439; A61B 2017/3443; A61B 2017/345;

(Continued)

(56) References Cited

U.S. PATENT DOCUMENTS 4,379,457 A * 4/1983 Gravener ............. A61B 17/115
227/156
5,431,635 A * 7/1995 Yoon .................. A61B 10/0233
604/164.12

(Continued)

FOREIGN PATENT DOCUMENTS

| CN | 208911220 U | 5/2019 |
| CN | 210750464 U | 6/2020 |
| CN | 210992506 U | 7/2020 |

OTHER PUBLICATIONS

BioSpace, "Thoracic Drainage Devices Market: Favorable Healthcare Policies to Create Promising Growth Scenario" <https://www.biospace.com/article/thoracic-drainage-devices-market-favorable-healthcare-policies-to-create-promising-growth-scenario> May 14, 2020.

(Continued)

*Primary Examiner* — Tan-Uyen T Ho

*Assistant Examiner* — Bridget E. Rabaglia

(74) *Attorney, Agent, or Firm* — MICHAEL BEST & FRIEDRICH LLP

(57) ABSTRACT

A device for accessing a cavity includes a tube and a trocar. The trocar extends through the tube and includes a handle, a sheath, and a tip member. The sheath is opposite the handle. The tip member is disposed in the sheath. The tip member is biased in an extension direction away from the handle. The tip member also includes an indicator indicating a position of the tip member relative to the handle.

20 Claims, 31 Drawing Sheets

(58) Field of Classification Search
   CPC .............. A61B 17/347; A61B 17/3474; A61B
                        17/3478; A61B 17/3494
   See application file for complete search history.

(56) References Cited

U.S. PATENT DOCUMENTS

| | | | |
|---|---|---|---|
| 10,786,148 | B2 | 9/2020 | Aho et al. |
| 2017/0245890 | A1* | 8/2017 | Ochi ..................... A61B 1/0684 |
| 2018/0333559 | A1 | 11/2018 | Makey |
| 2020/0113428 | A1* | 4/2020 | Shabana ............ A61B 1/00142 |
| 2020/0246105 | A1* | 8/2020 | Levesque ............... A61B 34/35 |
| 2021/0212722 | A1* | 7/2021 | Kiev .................. A61B 17/3415 |
| 2022/0211263 | A1* | 7/2022 | Norton ................. A61B 1/3132 |

OTHER PUBLICATIONS

Cardinal Health, "Chest Drainage Systems & Units," <https://www.cardinalhealth.com/en/product-solutions/medical/surgical/cardiothoracic/chest-drainage.html> webpage publicly available on or before Apr. 11, 2020.

Drumheller et al., "Comparison of a novel, endoscopic chest tube insertion technique versus the standard, open technique performed by novice users in a human cadaver model: a randomized, crossover, assessor-blinded study," Scand J trauma Resuc Emerg Med, 2018, 26(1): 110.

Getinge, "Pleuraguide Chest Tube Insertion Kit," <https://www2.getinge.com/us/product-catalog/pleuraguide-chest-tube-insertion-kit/> webpage publicly available on or before Aug. 14, 2020.

Hernandez et al., "Visually guided tube thoracostomy insertion comparison to standard of care in a large animal model," Injury, 2017, 48(4): 849-853.

Katballe et al., "A Novel Device for Accurate Chest Tube Insertion: A Randomized Controlled Trial," Ann Thorac Surg, 2016, 101(2): 527-532.

Medela, "Chest Drainage," <https://www.medelahealthcare.com/en-US/solutions/chest-drainage> webpage publicly available on or before Jan. 18, 2021.

Merit Medical, "Aspira Drainage System," <https://www.merit.com/peripheral-intervention/drainage/complete-solutions/aspira-drainage-system/> webpage publicly available on or before Sep. 27, 2020.

Penn Center for Innovation, "Guidance device for optimized directional placement of chest tubes," <https://upenn.technologypublisher.com/technology/34676> webpage publicly available on or before Sep. 20, 2020.

Science Daily, "New device shortens chest-tube insertion from minutes to seconds," <https://www.sciencedaily.com/releases/2016/03/160309094602.htm#> Mar. 9, 2016.

Teleflex, "Chest Drainage," <https://www.teleflex.com/usa/en/product-areas/surgical/cardiovascular/chest-drainage/index.html> webpage publicly available on or before Apr. 21, 2022.

Uresil, "Drainage Systems Accessories," <https://uresil.com/drainage-systems-accessories/> webpage publicly available on or before Jun. 12, 2018.

Utter, "The Rate of Pleural Fluid Drainage as a Criterion for the Timing of Chest Tube Removal: Theoretical and Practical Considerations," Ann Thorac Surg, 2013, 96: 2262-2267.

* cited by examiner

DEVICE AND METHOD FOR ACCESSING A CAVITY

RELATED APPLICATIONS

This application claims priority to U.S. Provisional Application No. 63/342,672, filed on May 17, 2022, the entire contents of which are hereby incorporated by reference.

FIELD

Embodiments described herein relate to devices and methods for accessing a cavity in a subject, and more specifically to devices and methods for accessing a thoracic cavity in a subject.

BACKGROUND

Tube thoracostomy is a potentially life-saving procedure performed by providers across multiple disciplines. Although it is a relatively minor procedure, it is associated with high complication rates. Currently, the standard method for placing a thoracostomy tube requires invasive procedures and blind placement of the tube into the chest.

Several key maneuvers must be completed during standard of care insertion of a thoracostomy tube (TT). First, the correct location for placement must be identified. Second, there is a sharp and blunt dissection of the thoracic wall. Third, a digit or instrument is inserted into the wall, and the pleural space is assessed for access to the cavity. Fourth, blind TT insertion is performed into the pleural space. Complications can occur during all four steps but are most common during the insertion maneuver. A sub-optimally placed tube can prevent drainage of the pleural cavity and often requires replacement. Moreover, TT insertion outside the thoracic cavity or into organ tissues can cause extreme complications.

Accordingly, there is an ongoing need for improved devices and methods for thoracic trocar placement.

SUMMARY

In one aspect, embodiments disclosed herein relate to a device for accessing a cavity. The device includes a tube and a trocar. The trocar extends through the tube and includes a handle, a sheath, and a tip member. The sheath is opposite the handle. The tip member is disposed in the sheath. The tip member is biased in an extension direction away from the handle. The tip member also includes an indicator indicating a position of the tip member relative to the handle.

In another aspect, embodiments disclosed herein relate to a device for accessing a cavity. The device includes a tube and a trocar. The trocar extends through the tube and includes a handle, a power source, an indicator light source, a sheath, a tip member, a photoresistor, a utility light source, and a light shield. The power source is disposed in the handle. The indicator light source is also disposed in the handle. The indicator light source is electrically coupled to the power source and projects light outside of the handle. The sheath is opposite the handle. The tip member is disposed in the sheath and is biased in an extension direction away from the handle. The tip member includes a distal end opposite the handle. The photoresistor is disposed in the tip member nearer to the distal end of the tip member than to the handle. The photoresistor is electrically coupled to the power source and to the indicator light. The utility light source is disposed in the tip member between the handle and the photoresistor. The utility light source is electrically coupled to the power source. The light shield is disposed between the photoresistor and the utility light source to direct light from the utility light source around the photoresistor and out the distal end of the tip member.

In another aspect, embodiments disclosed herein relate to a device for accessing a cavity. The device includes a tube and a trocar. The trocar extends through the tube and includes a handle, a sheath, a tip member, a camera, and an electronic port. The sheath is opposite the handle. The tip member is disposed in the sheath and is biased in an extension direction away from the handle. The tip member includes a distal end opposite the handle. The camera is disposed in the tip member nearer to the distal end of the tip member than to the handle. The camera is directed toward the distal end of the tip member. The electronic port is disposed in the handle and is electrically coupled to the camera.

DETAILED DESCRIPTION

Figure 1:
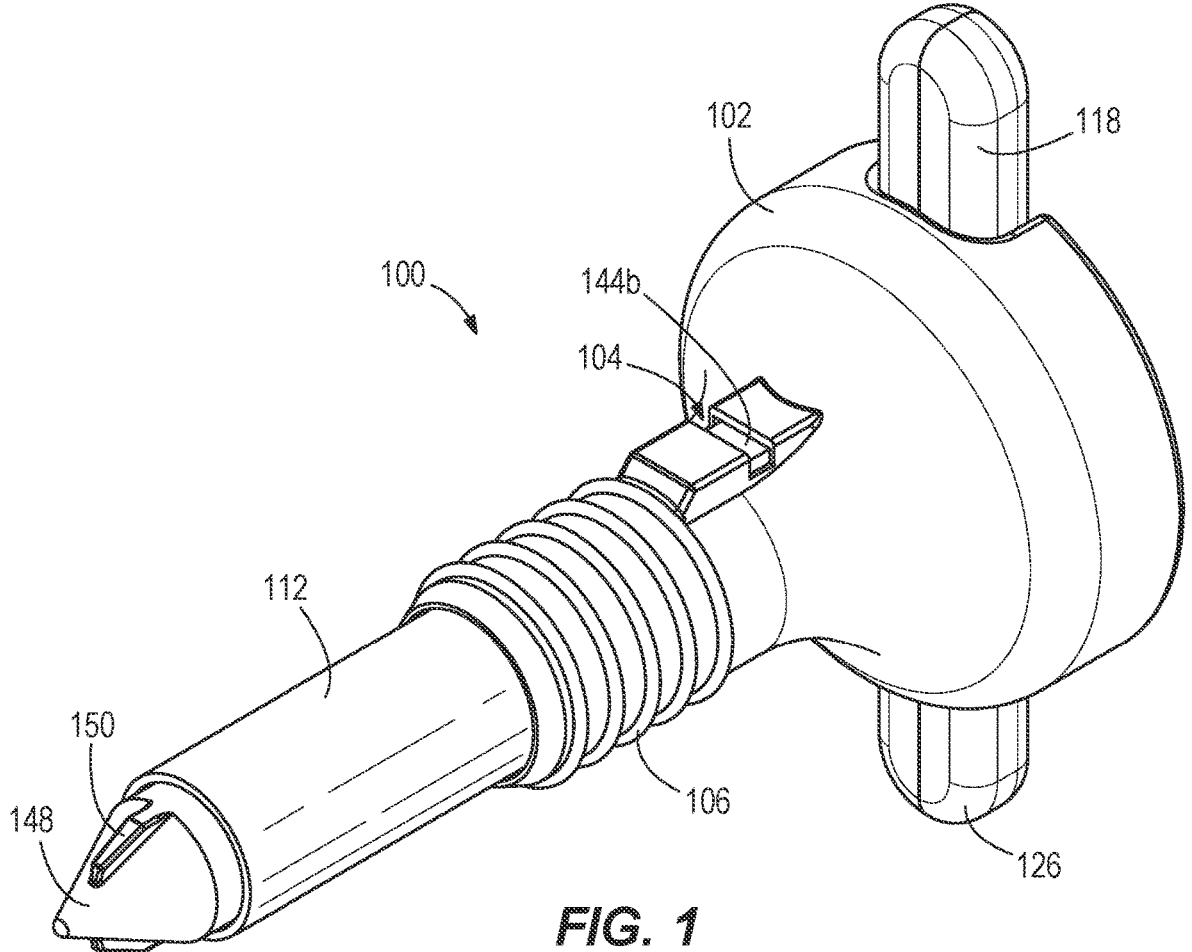
FIG. 1 illustrates a front perspective view of a device for accessing a cavity in a subject, according to embodiments disclosed herein.
Figure 2:
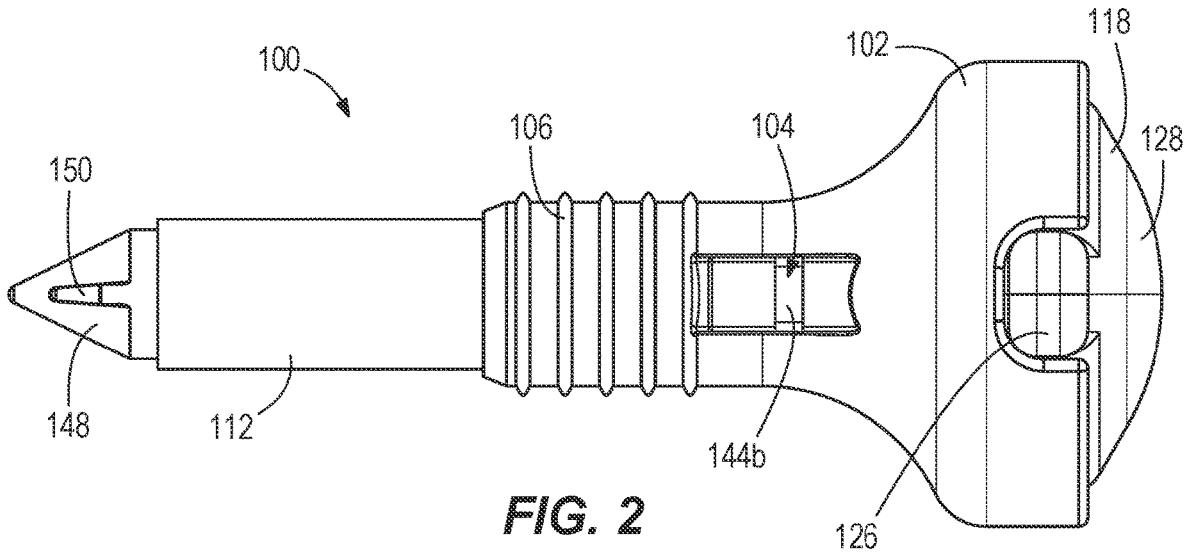
FIG. 2 illustrates a top plan view of the device of FIG. 1.

One or more embodiments are described and illustrated in the following description and accompanying drawings. These embodiments are not limited to the specific details provided herein and may be modified in various ways. Furthermore, other embodiments may exist that are not described herein.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Articles "a" and "an" are used herein to refer to one or to more than one (i.e., at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to expressly stated in this disclosure.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject comprises a human who is undergoing a procedure using a system or method as prescribed herein.

Unless otherwise defined, all technical terms used herein have the same meaning as commonly understood by one of ordinary skill in the art to which this disclosure belongs.

Embodiments of the present disclosure provide a surgical device that allows for simplified placement of a thoracostomy tube. The device allows for dissection into the chest under direct visualization, with no need for placement of the practitioner's finger into the chest. The device also allows for better positioning of the tube by directing it with the device itself.

Turning now to FIG. 1, a perspective view of a device 100 for accessing a cavity (e.g., thoracic cavity) in a subject is shown. The device 100 includes a sleeve 102 positioned as the outermost component of the device 100. In some embodiments, the sleeve 102 is made of a polymer. The sleeve 102 includes a slot 104 defined therein. As discussed in further detail below, the slot 104 allows a user to monitor a status of the device 100 during a procedure. The sleeve 102 further includes a plurality of raised sections (e.g., threads, ribs, bosses, or the like) 106. These ribs 106 function in some embodiments to slow further insertion of the device 100 through the chest wall, as the device 100 is close to its proper location at such a depth of insertion. In some embodiments, the ribs 106 function to hold (or anchor) the device 100 in place relative to the chest wall for the later steps of using the device 100 during the procedure.

Figure 6:
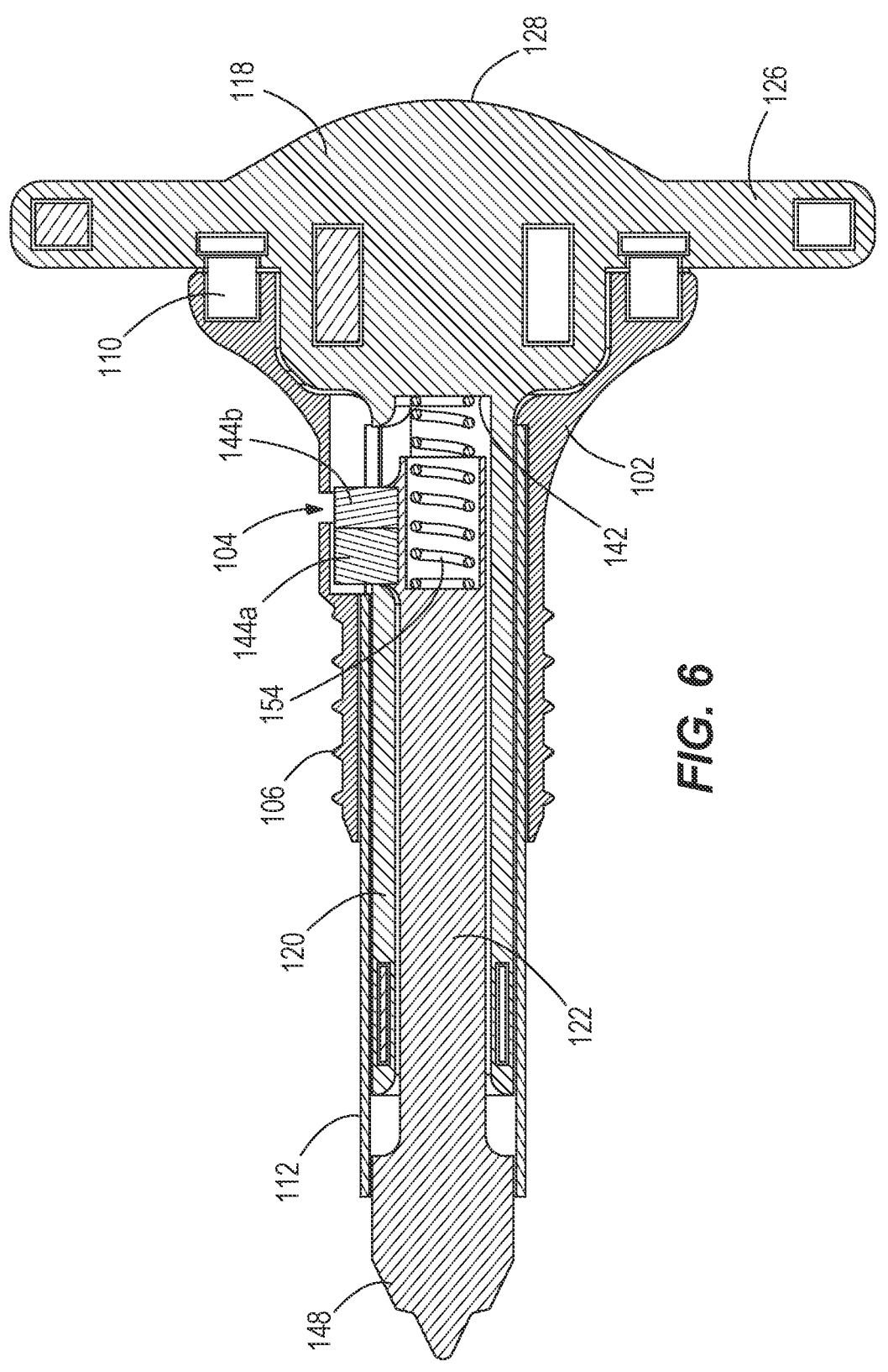
FIG. 6 illustrates a cross-sectional side elevation view of the device of FIG. 1 with the tip member in the extended position.
Figure 11:
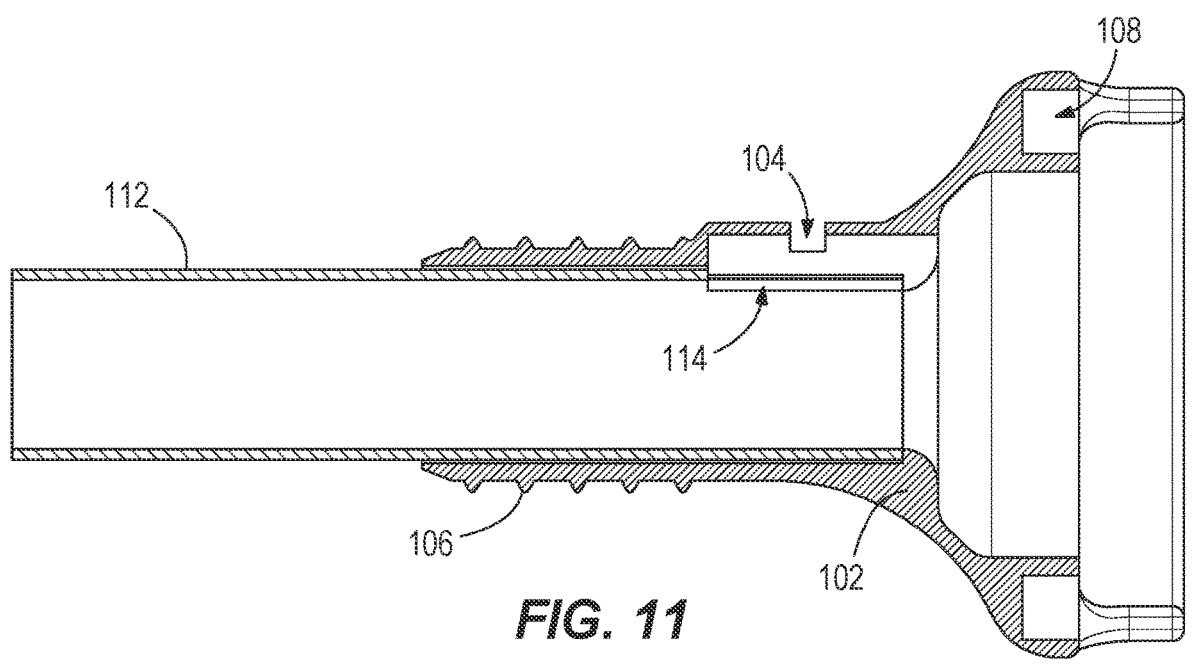
FIG. 11 illustrates a cross-sectional elevation view of the tube and sleeve of FIG. 9.
Figure 12:
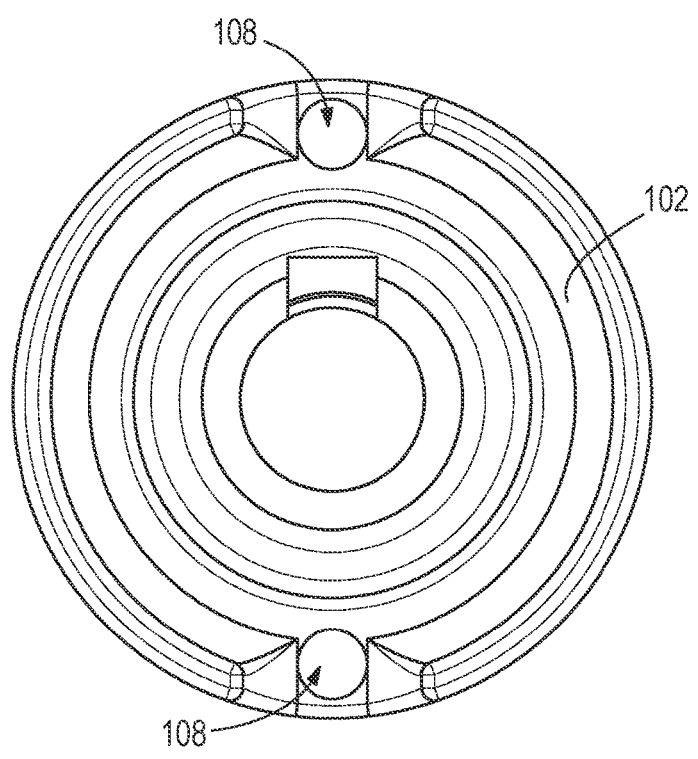
FIG. 12 illustrates a rear elevation view of the tube and sleeve of FIG. 9.

With reference to FIGS. 11 and 12, the sleeve 102 includes recesses 108 defined therein. As shown in FIG. 6, each recess 108 receives a corresponding plug 110 for removably connecting the sleeve 102 to another component discussed in more detail below. In some embodiments, the plugs 110 may be made of a material that is softer than the sleeve 102, such that the plugs 110 flex for ease of removal from the sleeve 102 with an appropriate pulling force by the user. The plugs 110 should be stiff enough such that the pulling force required is significant enough to prevent accidental removal of the plugs 110 from the recesses 108 of the sleeve 102 during the procedure.

Figures 9, 10:
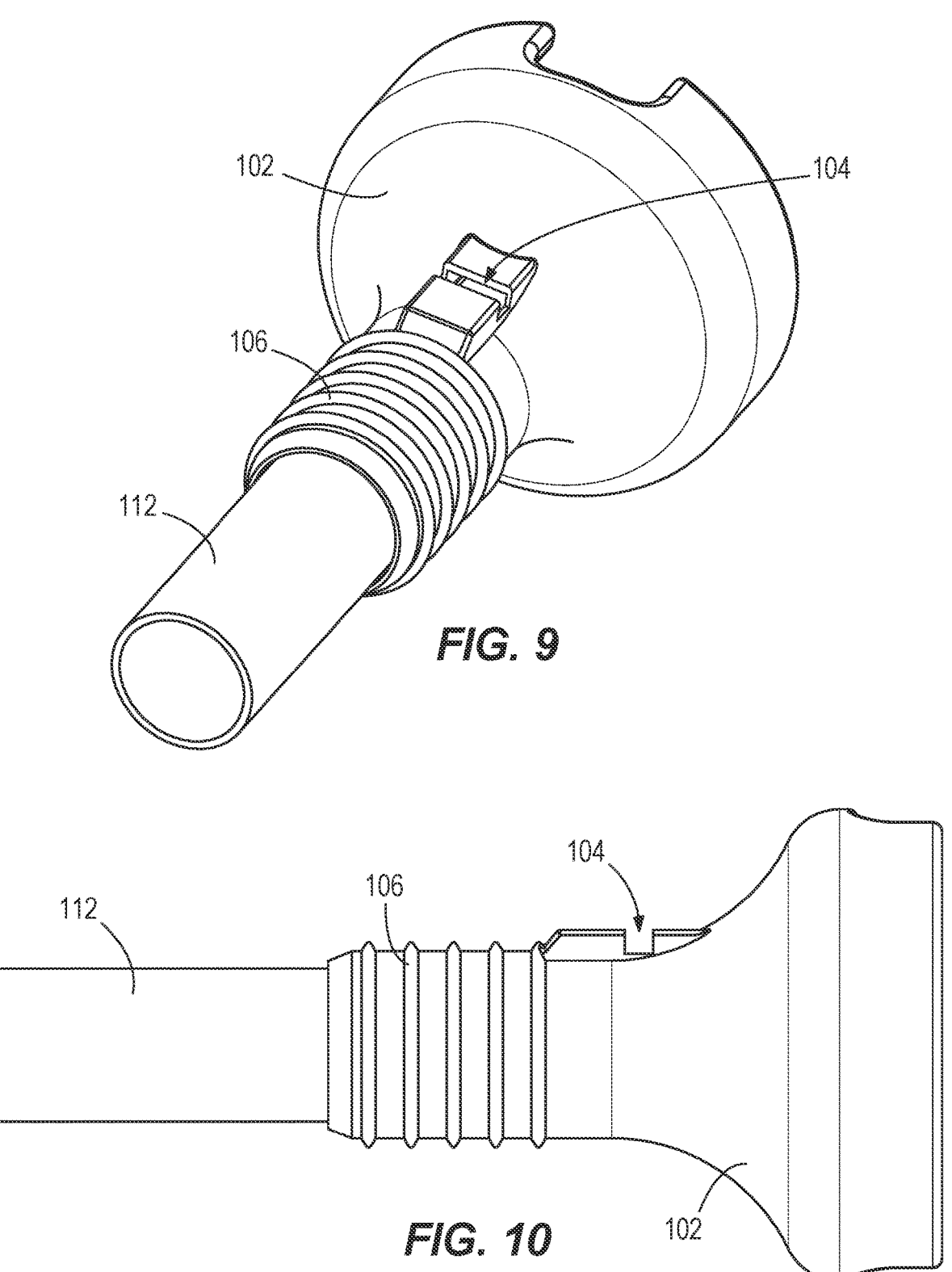
FIG. 9 illustrates a front perspective view of a tube and sleeve of the device of FIG. 1.
FIG. 10 illustrates a side elevation view of the tube and sleeve of FIG. 9.

Turning to FIG. 9, a tube 112 is disposed in the sleeve 102. In some embodiments, the tube 112 is made of metal. In some embodiments, the sleeve 102 may be overmolded onto the tube 112. As shown in FIG. 11, the tube 112 further includes a notch 114 defined therein. At least a portion of the notch 114 is generally aligned with the slot 104 defined in the sleeve 102. The tube 112 and the sleeve 102 are configured to remain in the chest wall while other components of the device 100 are removed, which will be discussed in further detail below. The tube 112 is rigid enough to maintain its shape during insertion through the chest wall.

Figures 4, 5:
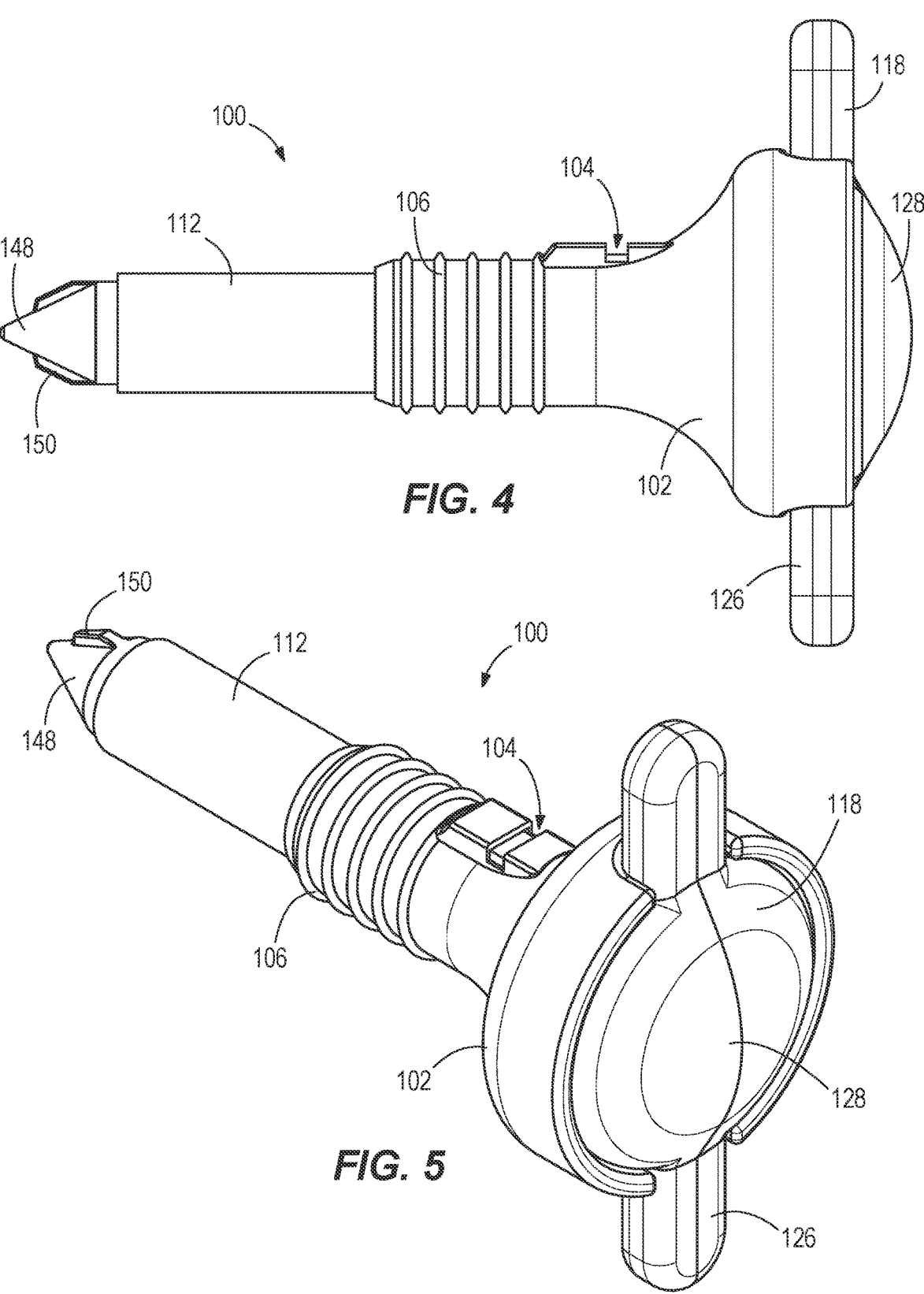
FIG. 4 illustrates a side elevation view of the device of FIG. 1.
FIG. 5 illustrates a rear perspective view of the device of FIG. 1.

Returning to FIG. 6, the device 100 further includes a trocar disposed in and extending through the tube 112. The trocar includes a handle 118, a sheath 120, and a tip member 122. The handle 118 includes recesses 124 (shown in FIG. 13) defined therein that correspond to the recesses 108 of the sleeve 102. As shown in FIG. 6, the plugs 110 couple the handle 118 to the sleeve 102. The plugs 110 are retained in the handle 118 such that the plugs 110 remain connected to the handle 118 upon separation of the handle 118 and the sleeve 102. As best shown in FIG. 5, the handle 118 includes two wings 126 for ease of grip for the user. The handle 118 may include more or fewer wings 126 in other embodiments, or the handle 118 may include protrusions of any shape to aid in the ergonomic handling of the handle 118. The handle 118 further includes a rounded butt 128 for ergonomic engagement with a user's palm.

Figure 13:
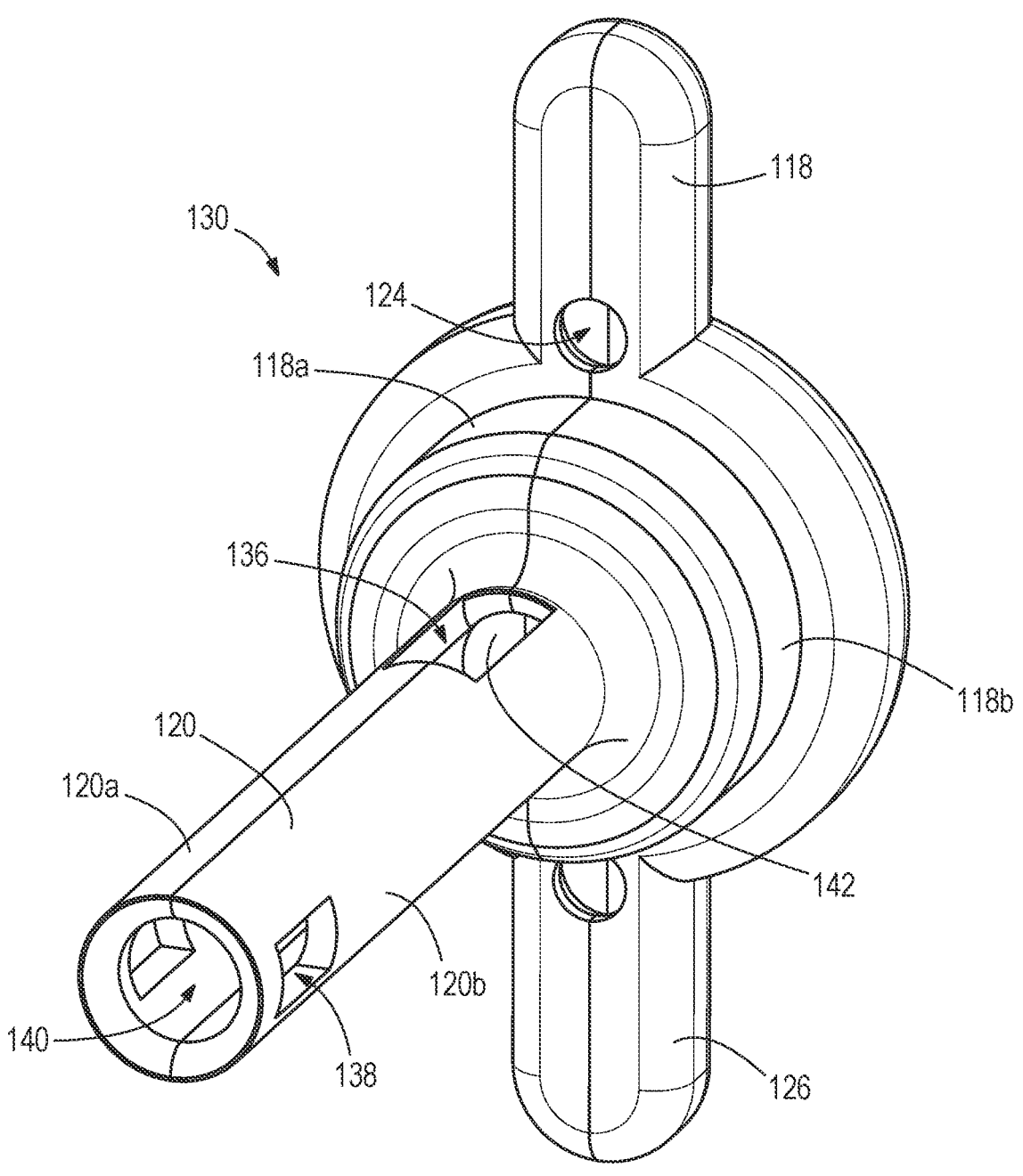
FIG. 13 illustrates a front perspective view of a handle and sheath of the device of FIG. 1.
Figures 14, 15:
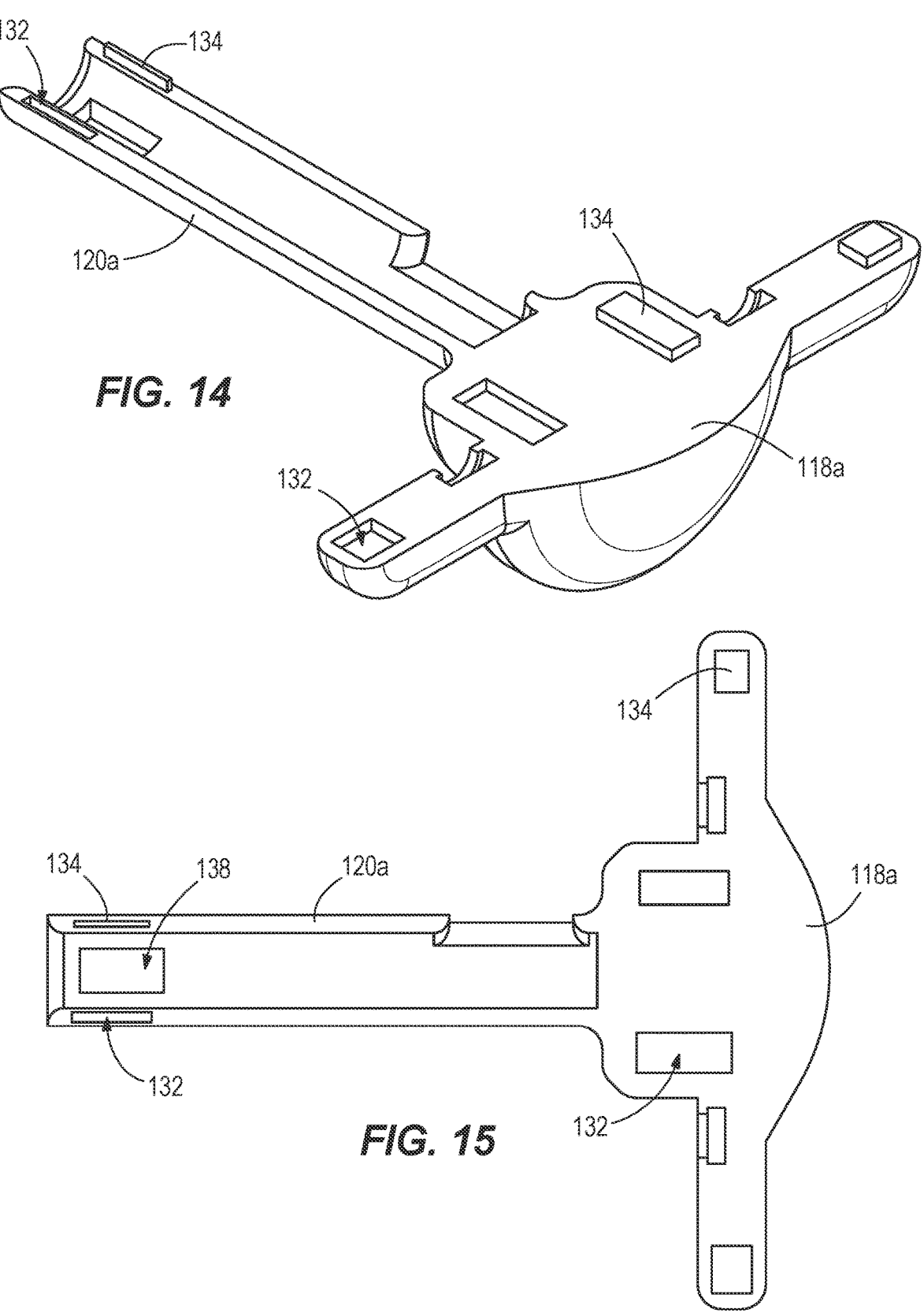
FIG. 14 illustrates a rear perspective view of one half of the handle and sheath of FIG. 13.
FIG. 15 illustrates a side elevation view of the one half of the handle and sheath of FIG. 13.

Turning now to FIGS. 13 and 14, some embodiments of the handle 118 and sheath 120 of the trocar may be in the form of a two-part assembly 130. In such embodiments, each half of the handle 118a, 118b is formed as a single, unitary part with the corresponding half of the sheath 120a, 120b. In some embodiments, each half of the assembly 130 is identical to the other half in order to reduce the complexity of manufacturing the assembly 130. For instance, each half of the handle 118a, 118b and/or sheath 120a, 120b may include an indentation 132 and a protrusion 134 such that the protrusion 134 of one half 118a, 118b and/or 120a, 120b is received in the corresponding indentation 132 of the other half 118b, 118a and/or 120b, 120a. The protrusions 134 and indentations 132 may be sized such that the halves of the two-part assembly 130 snap-fit together.

With continued reference to FIG. 13, the sheath 120 is positioned opposite the handle 118. The sheath 120 includes an opening 136 defined therein. At least a portion of the opening 136 is generally aligned with the notch 114 of the tube 112 and with the slot 104 of the sleeve 102. The sheath 120 further includes one or more channels 138 defined therein. In the illustrated embodiment, the channels 138 are two diametrically opposed channels 138 in the cylindrical sheath 120 near the end of the sheath 120 opposite the handle 118. The sheath 120 further includes an interior passage 140 defined therein that is terminated at an end wall 142 adjacent the handle 118.

Figures 16, 17, 18:
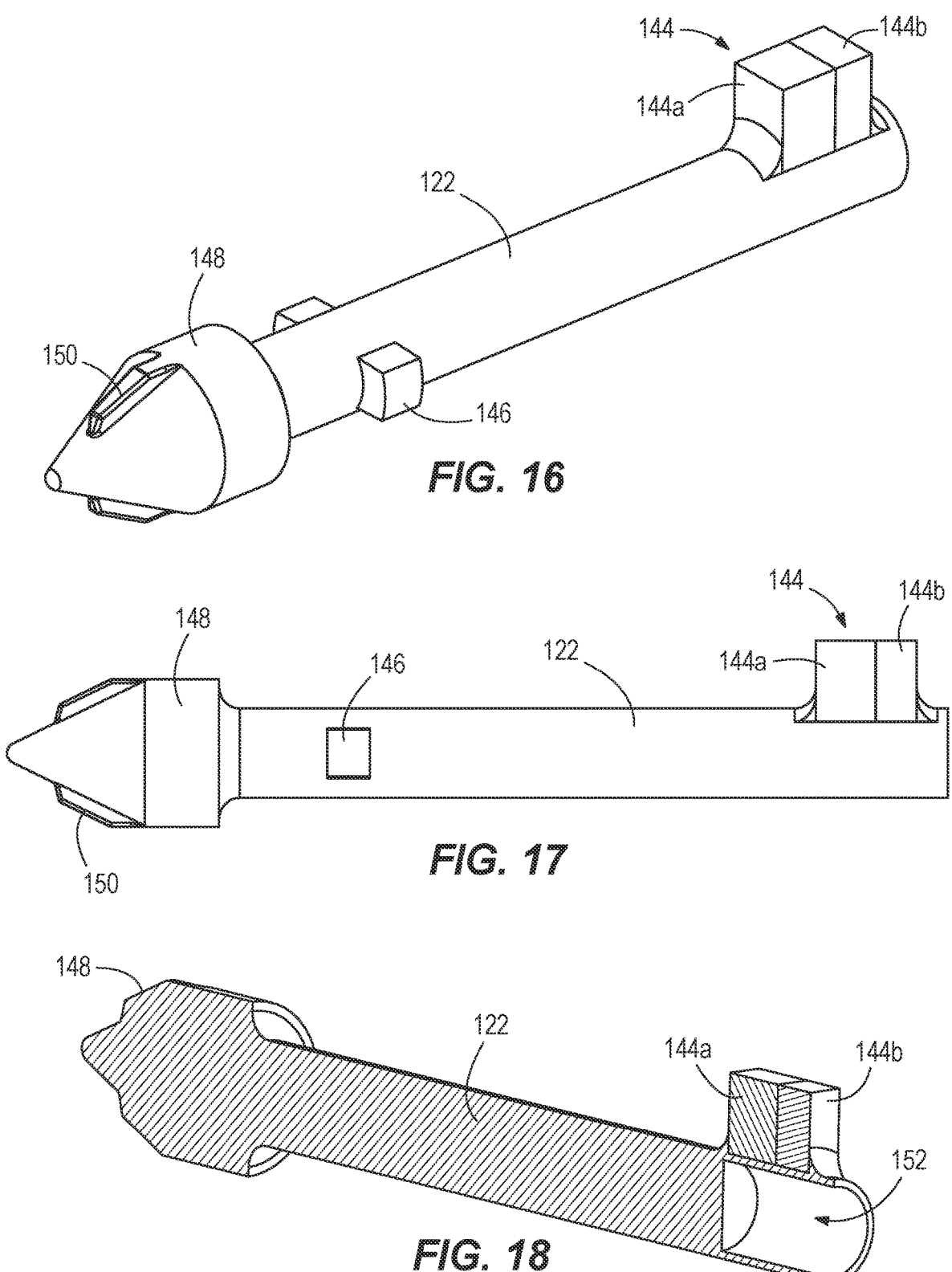
FIG. 16 illustrates a front perspective view of a tip member of the device of FIG. 1.
FIG. 17 illustrates a side elevation view of the tip member of FIG. 16.
FIG. 18 illustrates a cross-sectional rear perspective view of the tip member of FIG. 16.

As best shown in FIG. 16, the device 100 further includes the tip member 122. The tip member 122 includes an indicator 144 disposed near a proximal end of the tip member 122. In the illustrated embodiment, the indicator 144 includes two indicator sections 144a, 144b (e.g., a retracted section and an extended section, respectively). The two indicator sections 144a, 144b may have differing appearances including, for instance, different colors to indicate to the user whether the device 100 is properly located in the thoracic cavity. In the illustrated embodiment, the retracted section 144a is red or orange and the extended section 144b is green. In some embodiments, one or more of the indicator sections 144a, 144b may be configured to glow in the dark and/or be highly reflective of incoming light. The indicator 144 is positioned to be aligned with and visible through the opening 136 in the sheath 120, the notch 144 in the tube 112, and the slot 104 in the sleeve 102 (shown in FIGS. 6-8). The tip member 122 further includes one or more protrusions 146 positioned to extend into the corresponding channel 138 in the sheath 120. The tip member 122 also includes a pointed tip 148 that is shaped to open and penetrate through an incision in the chest wall. The pointed tip 148 may include one or more fins 150. As shown in FIG. 18, the tip member 122 further includes a spring retention cavity 152 defined therein in the proximal end opposite the pointed tip 148.

Figure 3:
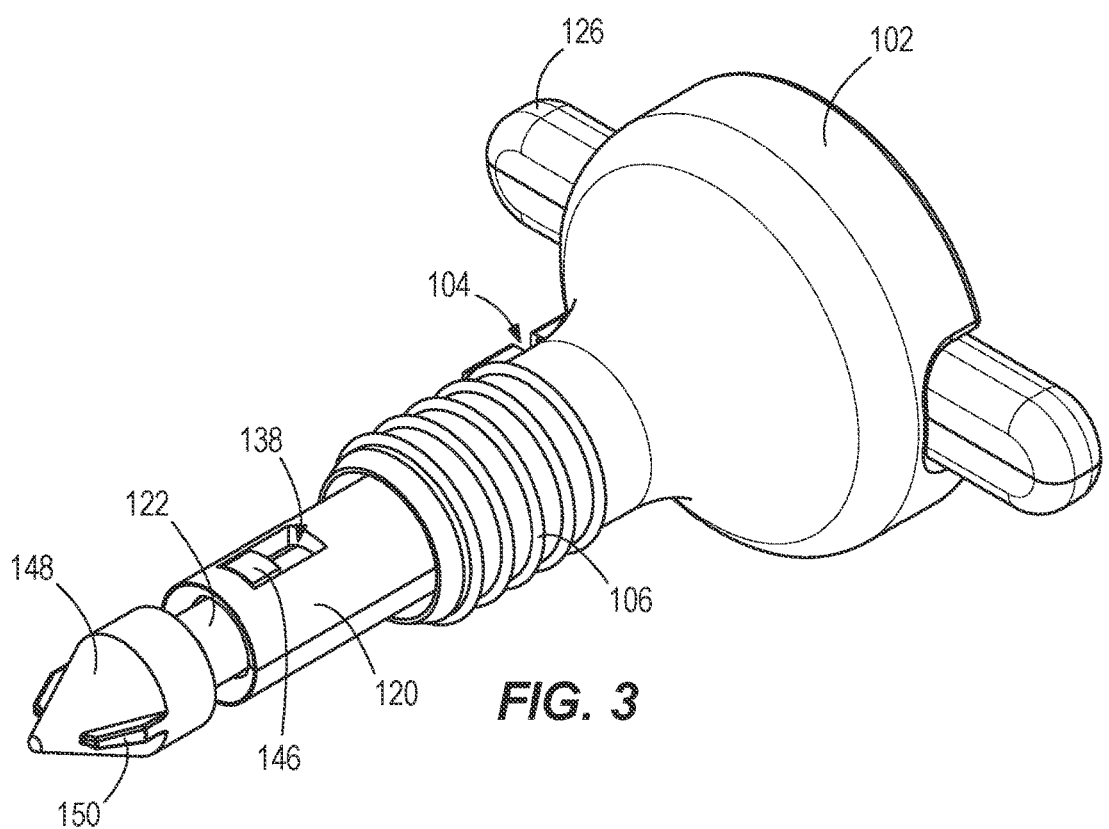
FIG. 3 illustrates a front perspective view of the device of FIG. 1 with the tube removed.
Figure 7:
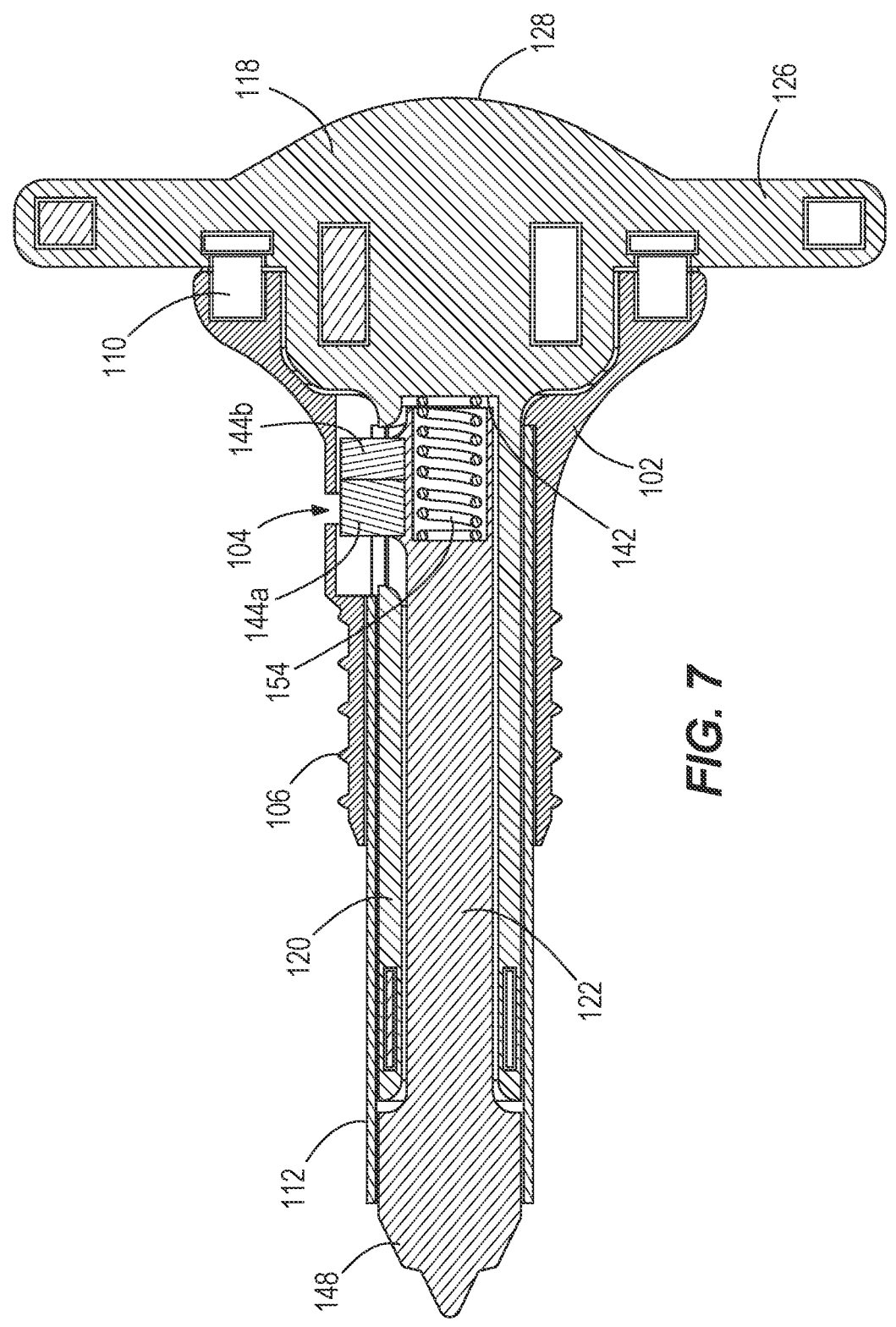
FIG. 7 illustrates a cross-sectional side elevation view of the device of FIG. 1 with the tip member in the retracted position.
Figure 8:
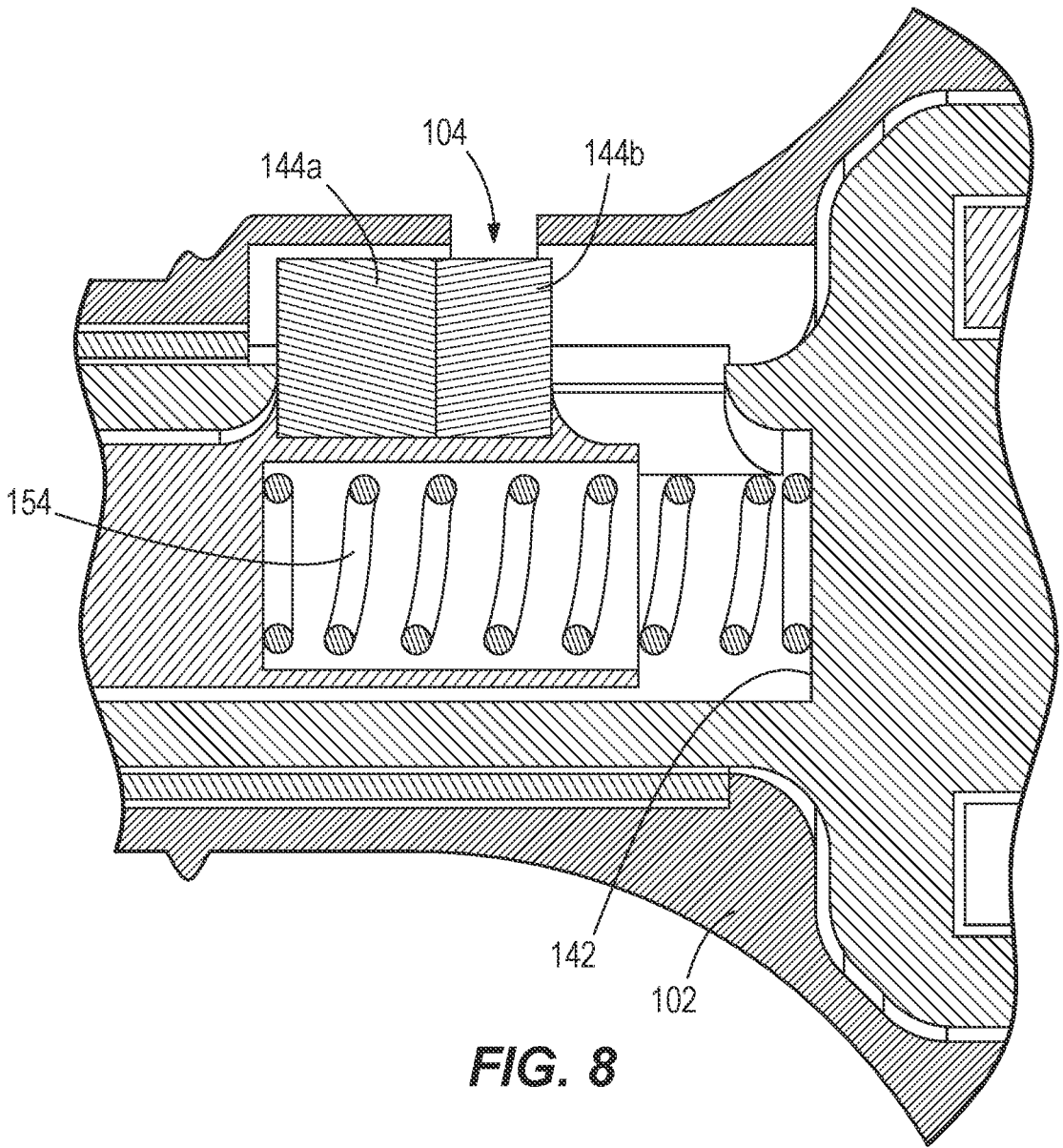
FIG. 8 illustrates a detailed cross-sectional side elevation view of the indicator of the device of FIG. 1 with the tip member in the extended position.

Turning now to FIG. 6, a cross-section of the assembled device 100 is shown. The tip member 122 is slidably received in the sheath 120 and biased away from the handle 118 by a bias (e.g., a coil spring) 154. As shown in FIG. 3, to maintain the tip member 122 in proper alignment with the sheath 120, the protrusions 146 of the tip member 122 are slidably received in the corresponding channels 138 in the sheath 120. Returning to FIG. 6, the coil spring 154 is at least partially disposed in the spring retention cavity 152 of the tip member 122 and engages the end wall 142 of the sheath 120. Forces on the pointed tip 148 can push the tip member 122 toward the handle 118 against the bias of the coil spring 154 (as shown in FIG. 7). In some embodiments, the coil spring 154 can have a spring constant that corresponds closely with the amount of force required to penetrate a human patient's chest wall. Further, the spring constant can be chosen such that engagement of the pointed tip 148 with the patient's liver, spleen, or the like would compress the spring 154. In this arrangement, the position of the tip member 122 relative to the sheath 120 and/or handle 118 is shown to a user by the indicator 144.

As shown in FIG. 6, if the tip member 122 is not pushed by the chest wall, a liver, a spleen, or the like, the extended section 144*b* of the indicator 144 is displayed to a user viewing the slot 104 of the sleeve 102. This extended section 144*b* being displayed as the device 100 is extending through the chest wall can indicate to the user that the device 100 is likely in a proper location in the thoracic cavity. Similarly, as shown in FIG. 7, if the tip member 122 is pushed with enough force, the retracted section 144*a* of the indicator 144 is displayed. The retracted section 144*a* being displayed as the device 100 is extending through the chest wall can indicate to the user that the pointed tip 148 is likely engaging a structure inside the thoracic cavity and the placement of the device 100 in the thoracic cavity is likely improper. The respective sections 144*a*, 144*b* of the indicator 144 are visible to the user due to the fact that the indicator 144 extends through the opening 136 of the sheath 120, extends through the notch 114 of the tube 112, and is aligned with the slot 104 of the sleeve 102.

To use the device 100, first, an incision is made in the chest between adjacent ribs (as is typical for a conventional tube thoracostomy). Once the incision is made, the pointed tip 148 of the tip member 122 is inserted into the incision. The tip member 122 spreads open the incision to allow further insertion of a portion of the tube 112 and a portion of the sleeve 102. The sleeve 102 can be inserted far enough that the raised sections 106 of the sleeve 102 engage with the chest wall to anchor the device 100 relative to the chest wall. If the extended section 144*b* of the indicator 144 is displayed through the slot 104 of the sleeve 102 (as shown in FIG. 6), the user can deduce that the placement of the device 100 is proper (typically, a desirable placement is anteriorly and apically, e.g., toward the patient's back and toward patient's head in the thoracic cavity). If the retracted section 144*a* of the indicator 144 is displayed through the slot 104 of the sleeve 102 (as shown in FIG. 7), the user then repositions the device 100 (e.g., pulls the device 100 slightly away from the patient, redirects the pointed tip 148 elsewhere in the thoracic cavity, or the like). Once the extended section 144*b* of the indicator 144 is displayed through the slot 104 of the sleeve 102 (as shown in FIG. 6), the trocar is then removed from the tube 112 and the sleeve 102 such that only the tube 112 and sleeve 102 remain in the chest wall. Next, a cannula is threaded through the sleeve 102 and the tube 112 into the thoracic cavity of the patient. Once the end of the cannula is placed in an appropriate location within the thoracic cavity, the sleeve 102 and tube 112 are removed by pulling the sleeve 102 and tube 112 over the remainder of the cannula that is outside the thoracic cavity.

The following embodiment of the device 200 shares many similarities with the embodiment of the device 100 described above. In the interest of brevity, not all components of the device 200 below will be described. Rather, only differences between the embodiments and/or further details not explored above will be described. Like components will be numbered the same as the corresponding components of the device 100 but increased by a value of one hundred.

Figure 19:
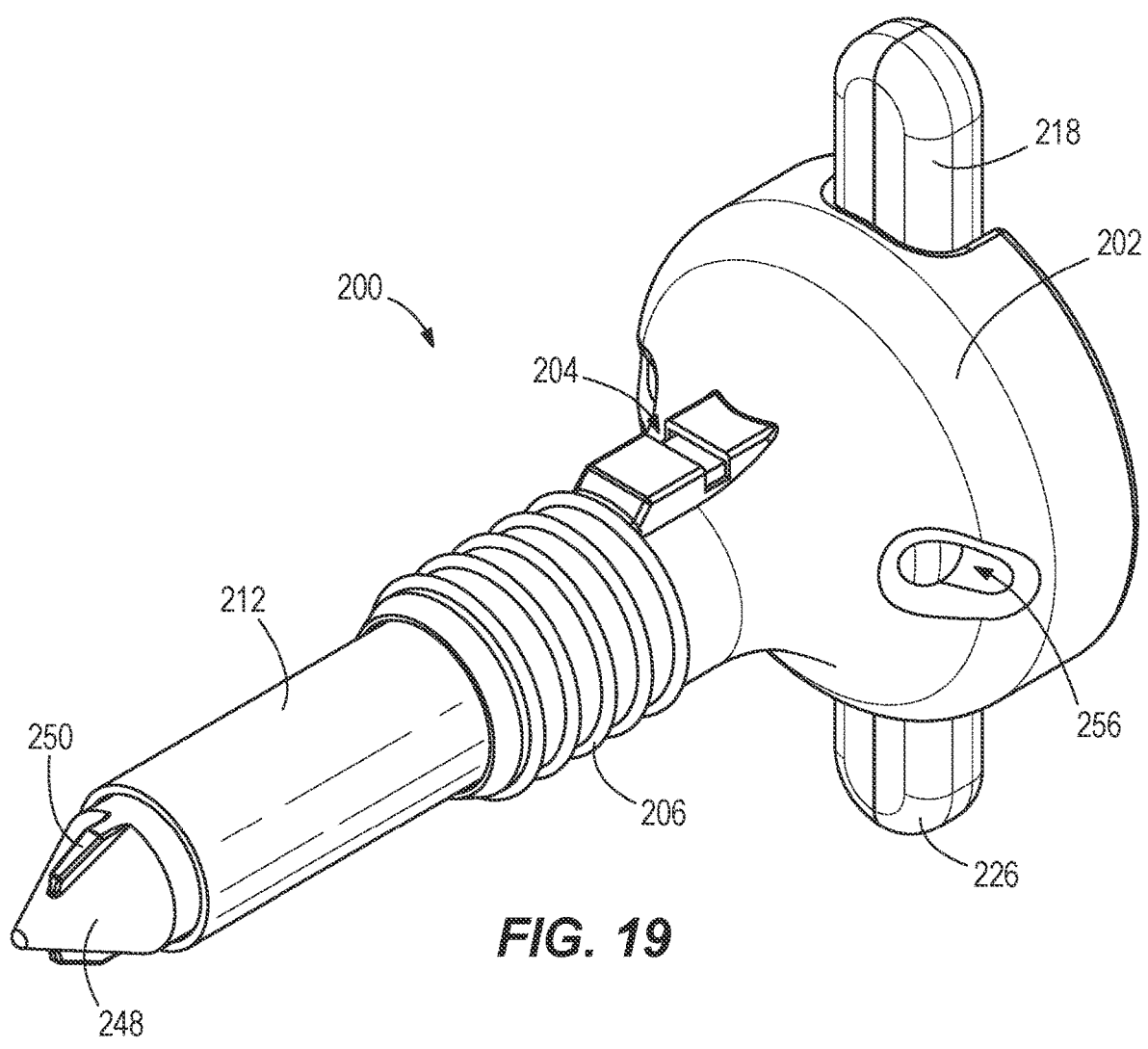
FIG. 19 illustrates a front perspective view of a device for accessing a cavity in a subject, according to embodiments disclosed herein.
Figure 20:
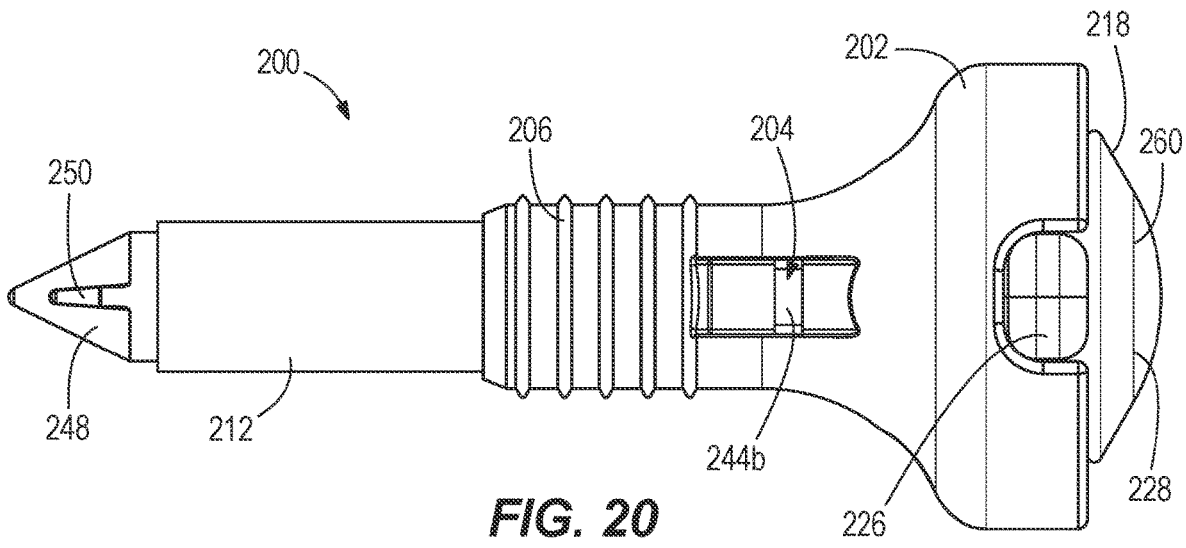
FIG. 20 illustrates a top plan view of the device of FIG. 19.
Figure 21:
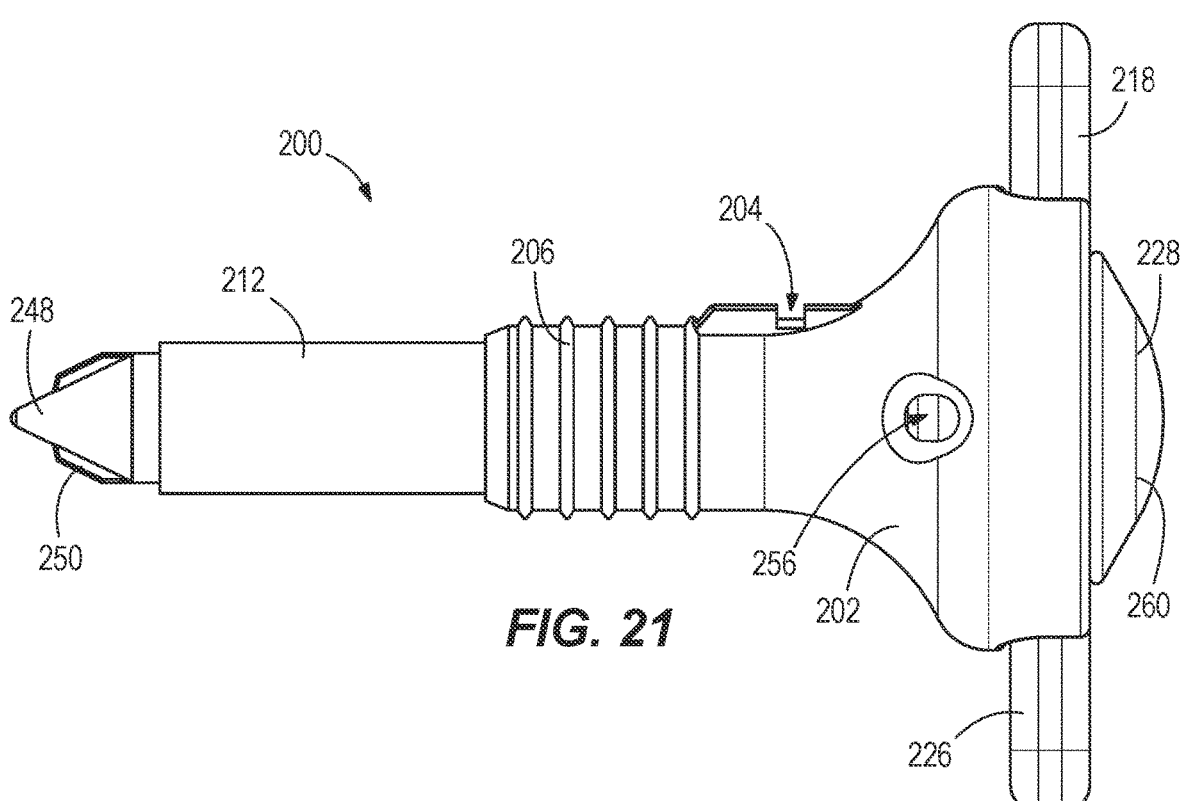
FIG. 21 illustrates a side elevation view of the device of FIG. 19.
Figure 22:
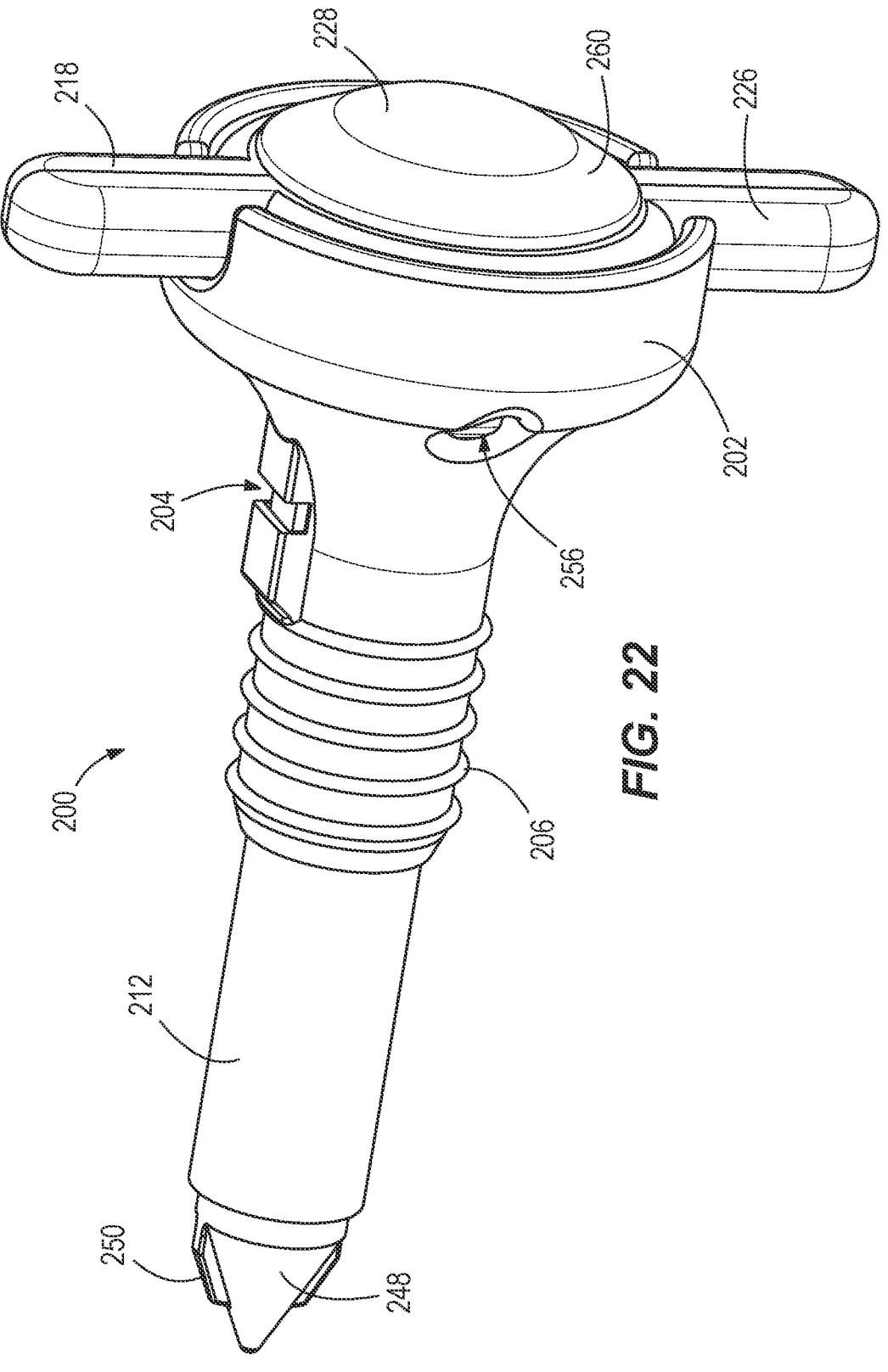
FIG. 22 illustrates a rear perspective view of the device of FIG. 19.

With reference to FIG. 19, another embodiment of a device 200 for accessing a thoracic cavity is shown. The sleeve 202 of the device 200 includes two diametrically opposed openings 256 for viewing light emitted from the device 200 as described in more detail below.

Figure 23:
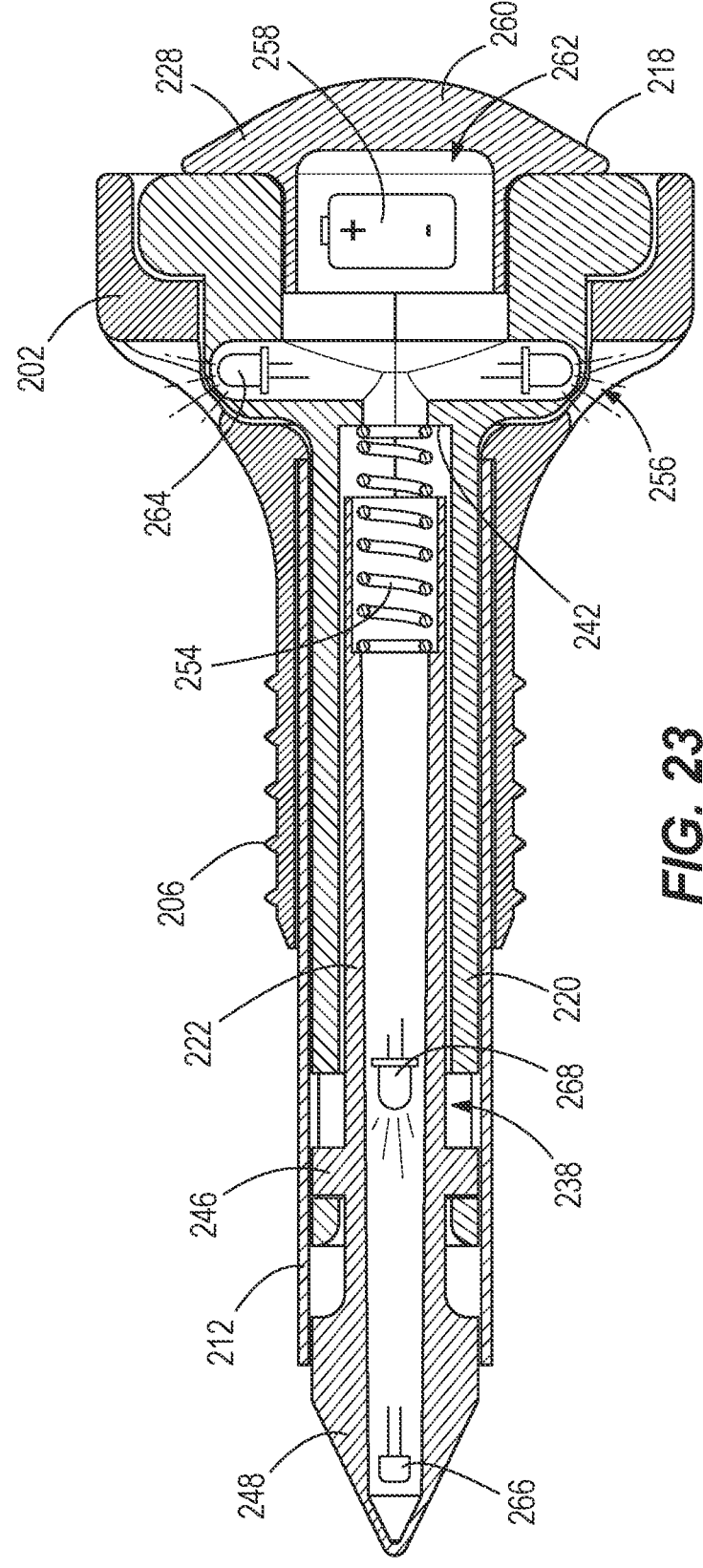
FIG. 23 illustrates a cross-sectional top plan view of the device of FIG. 19.
Figure 24:
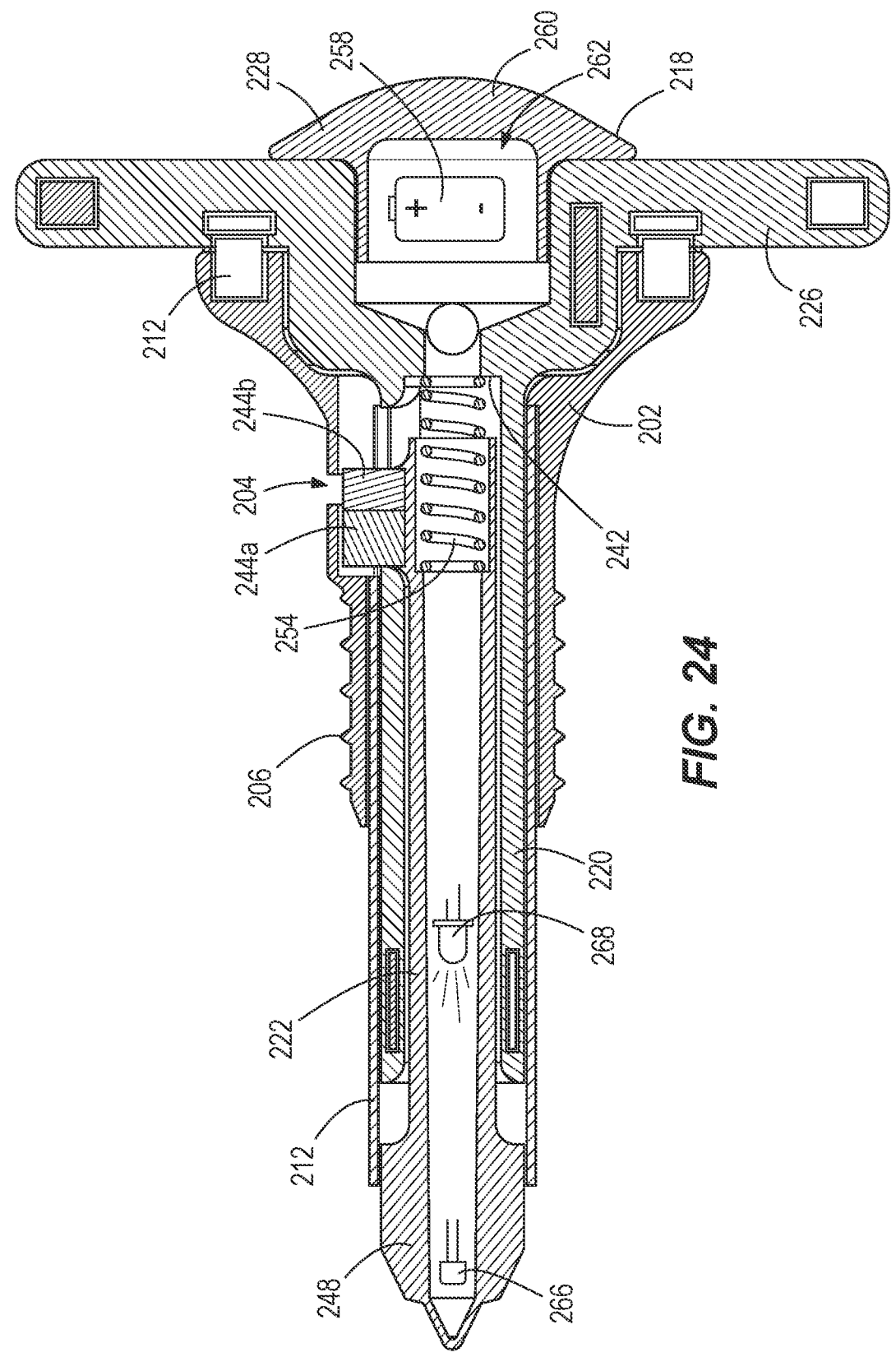
FIG. 24 illustrates a cross-sectional side elevation view of the device of FIG. 19.
Figure 25:
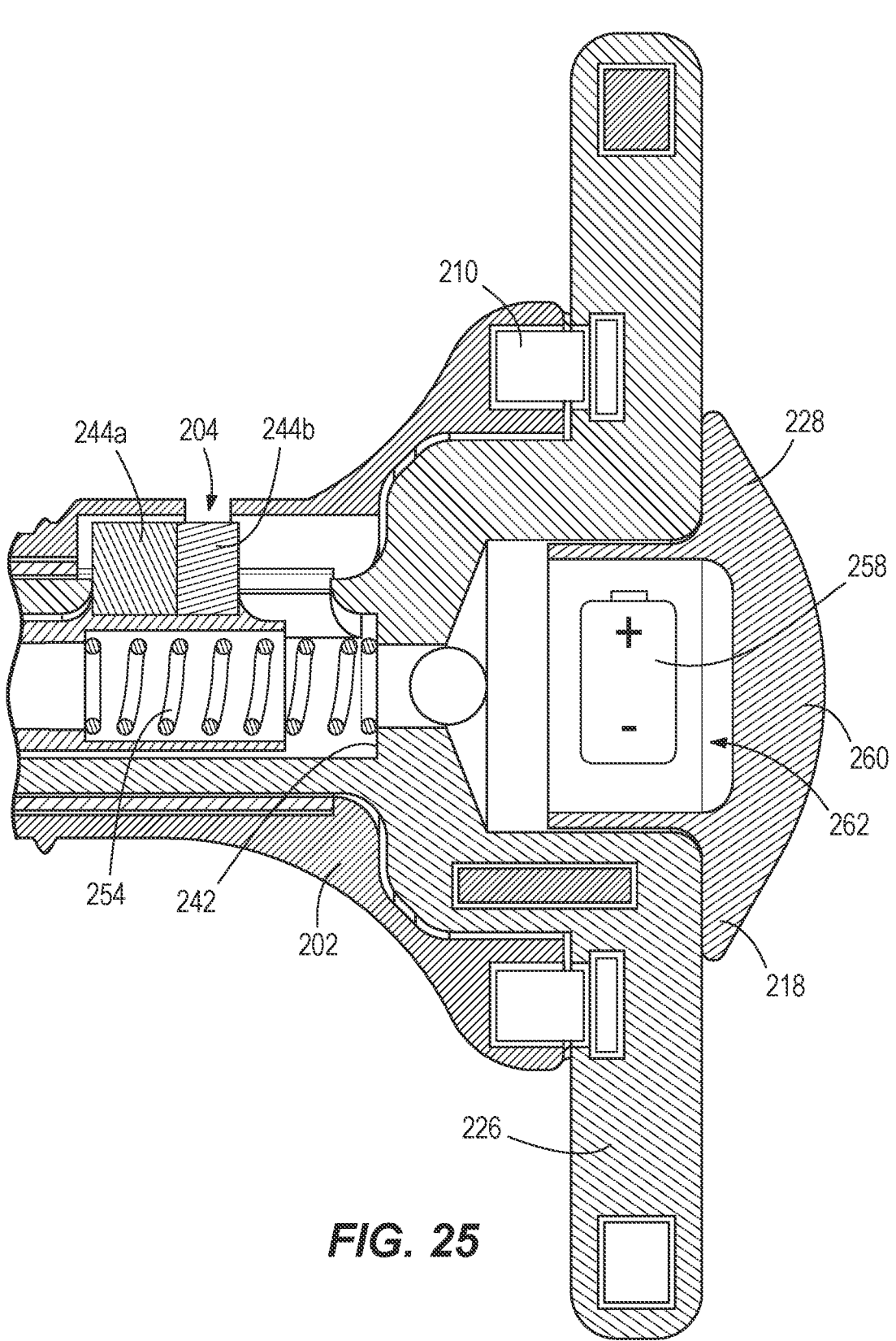
FIG. 25 illustrates a detailed cross-sectional side elevation view of the indicator and power source of the device of FIG. 19.
Figures 32, 33, 34:
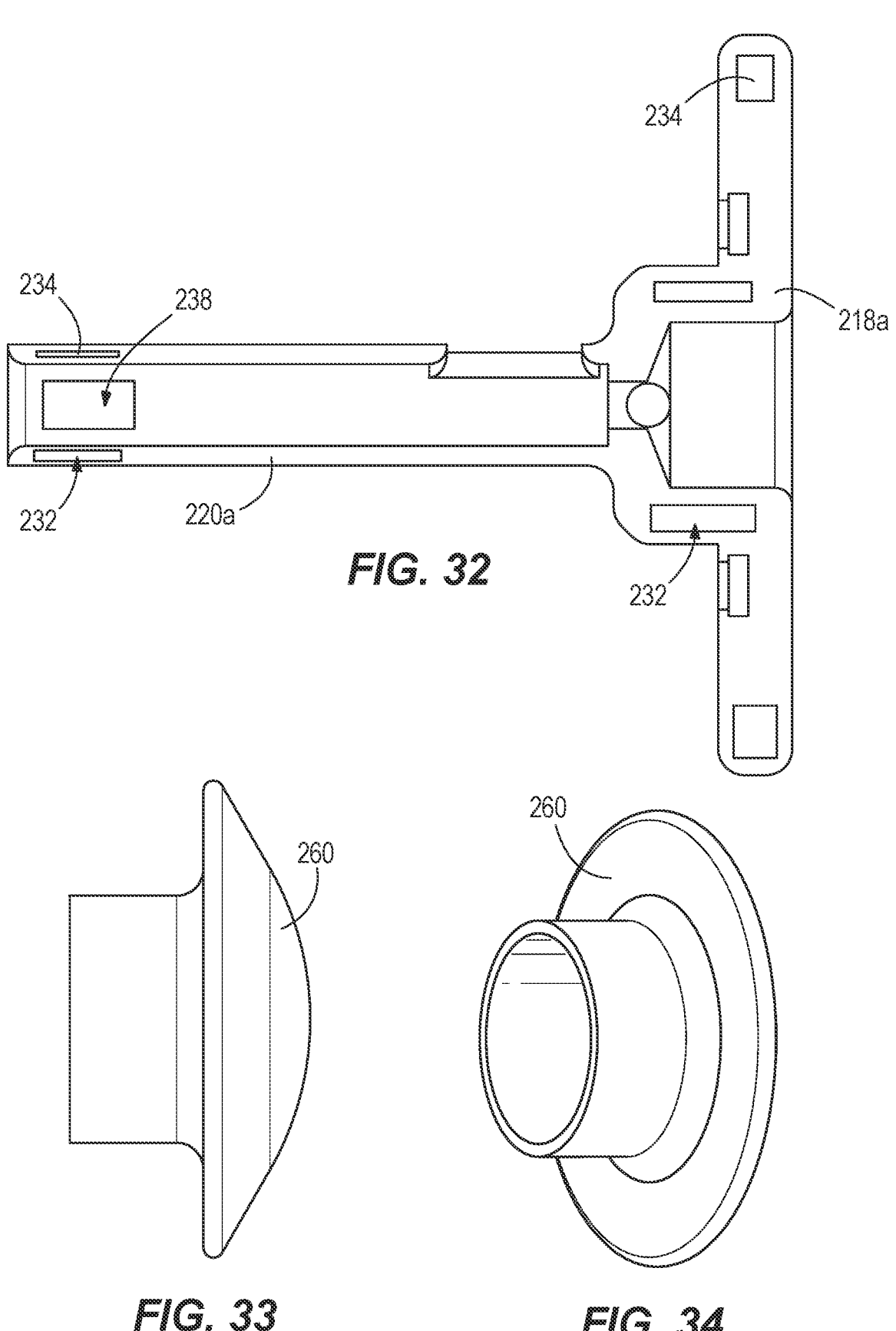
FIG. 32 illustrates a side elevation view of the one half of the handle and the sheath of FIG. 31.
FIG. 33 illustrates a side elevation view of a cap of the handle of the device of FIG. 19.
FIG. 34 illustrates a front perspective view of the cap of FIG. 33.
Figure 35:
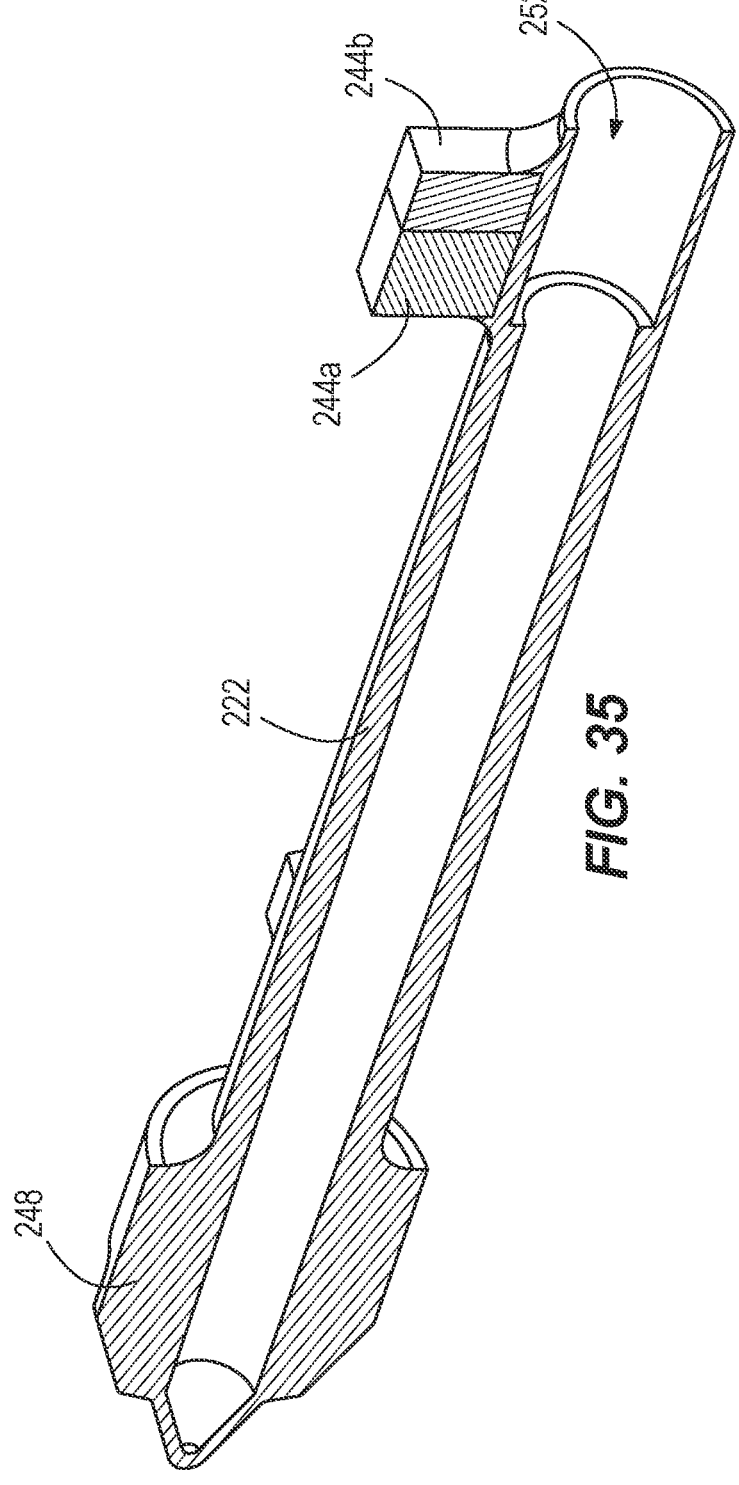
FIG. 35 illustrates a cross-sectional rear perspective view of a tip member of the device of FIG. 19.

Turning now to FIG. 23, a cross-section of the device 200 is shown. The trocar further includes a power source 258 disposed in the handle 218. The power source 258 may include, for instance, a lithium-ion battery. The power source 258 may be a primary battery (single use) or a secondary battery (rechargeable). The power source 258 may be accessible through a removable cap 260 of the handle 218. The cap 260 (shown alone in FIGS. 33 and 34) removably covers the power source 258 disposed in a power source cavity 262 that is defined in the handle 218. In some embodiments, the cap 260 is threadingly engaged with the handle 218. In other embodiments, such as the illustrated embodiment, the cap 260 may be dimensioned to have a press-fit or snap-fit with the opening of the power source cavity 262 of the handle 218. The cap 260 may be removable with a user's fingers and/or fingernails in some embodiments, but other embodiments may include the cap 260 being removable only with a tool (e.g., a screwdriver, a coin, or the like).

Returning to FIG. 23, the trocar further includes a plurality of indicator light sources 264 disposed in the handle 218. In the illustrated embodiment, the indicator light sources 264 include light-emitting diodes (LEDs). The indicator light sources 264 are coupled to the power source 258 and are configured to project light outside of the handle 218. In the illustrated embodiment, at least a portion of the handle 218 is made from a translucent material, such that the light from the indicator light sources 264 passes through a wall of the handle 218 to project outside of the handle 218. The openings 256 in the sleeve 202 are aligned with the respective indicator light sources 264 such that the light from the indicator light sources 264 also passes through the openings 256 to be visible to a user. In some embodiments, the handle 218 may be made from a transparent material. In still other embodiments, the handle 218 may be made from an opaque material while also including one or more holes defined therein to allow light to pass through the holes. Yet another embodiment may include the handle 218 having a thinner section of the side wall compared to other portions of the handle 218 such that the light is able to pass through the thinner section but not the other portions of the handle 218.

The trocar also includes a photoresistor 266 disposed in the tip member 222. The photoresistor 266 is adjacent the pointed tip 248 of the tip member 222. Stated another way, the photoresistor 266 is adjacent the distal end of the tip member 222. In some embodiments, the photoresistor 266 can be said to be disposed nearer to the distal end of the tip member 222 than to the handle 218. The photoresistor 266 is electrically coupled with the power source and with the indicator light source 264. "Electrically coupled," as used anywhere throughout the present disclosure, should be interpreted to mean any wired or wireless connection either directly between the two mentioned components or indirectly between the two mentioned components (via, for instance, a circuit board, bus bar, or other component). The photoresistor 266 is configured to change resistance for electricity passing through the photoresistor 266 based on how much light impinges on its measurement surface. Typically, a photoresistor has a lower resistance at relatively high light levels and a higher resistance at relatively low light levels. In the illustrated embodiment, the measurement surface of the photoresistor 266 is facing outwardly through the material of the pointed tip 248 of the tip member 222. In the illustrated embodiment, at least the pointed tip 248 of the tip member 222, therefore, is translucent. In some embodiments, at least the pointed tip 248 is transparent. Some embodiments include the entire tip member 222 formed of transparent acrylic or some other polymer. Based on how much light is received at the photoresistor 266 from an area forward and outside the pointed tip 248 of the tip member 222, the brightness of the indicator light sources 264 will vary. A user, therefore, can judge how close a surface (such as a structure inside the thoracic cavity) is to the pointed tip 248 based on an observation of the brightness of the indicator light sources 264.

The trocar further includes a utility light source 268 disposed in the tip member 222 between the handle 218 and the photoresistor 266. The utility light source 268 is electrically coupled to the power source 258. In some embodiments, the utility light source 268 may be configured to project light into the walls of the tip member 222 such that the light from the utility light source 268 enters the tip member 222 and travels through the tip member 222 via total internal reflection until the light reaches the pointed tip 248 of the tip member 222. In such embodiments, inclusions, surface roughness, or the like may be located on or in the pointed tip 248 such that the light from the utility light source is emitted outwardly from the pointed tip 248 away from the photoresistor 266. In the illustrated embodiment, however, the utility light source 268 projects light forward toward the distal end of the tip member 222 without intentional use of total internal reflection in the tip member 222.

Figure 26:
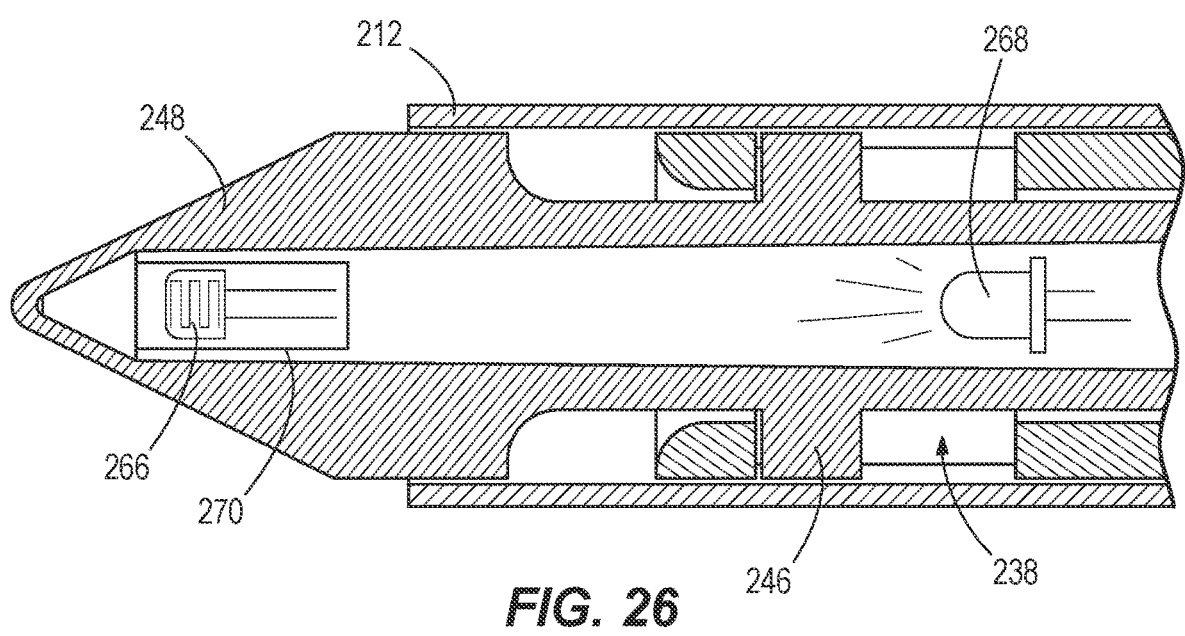
FIG. 26 illustrates a detailed cross-sectional side elevation view of the utility light source, light shield, and photoresistor of the device of FIG. 19.
Figure 27:
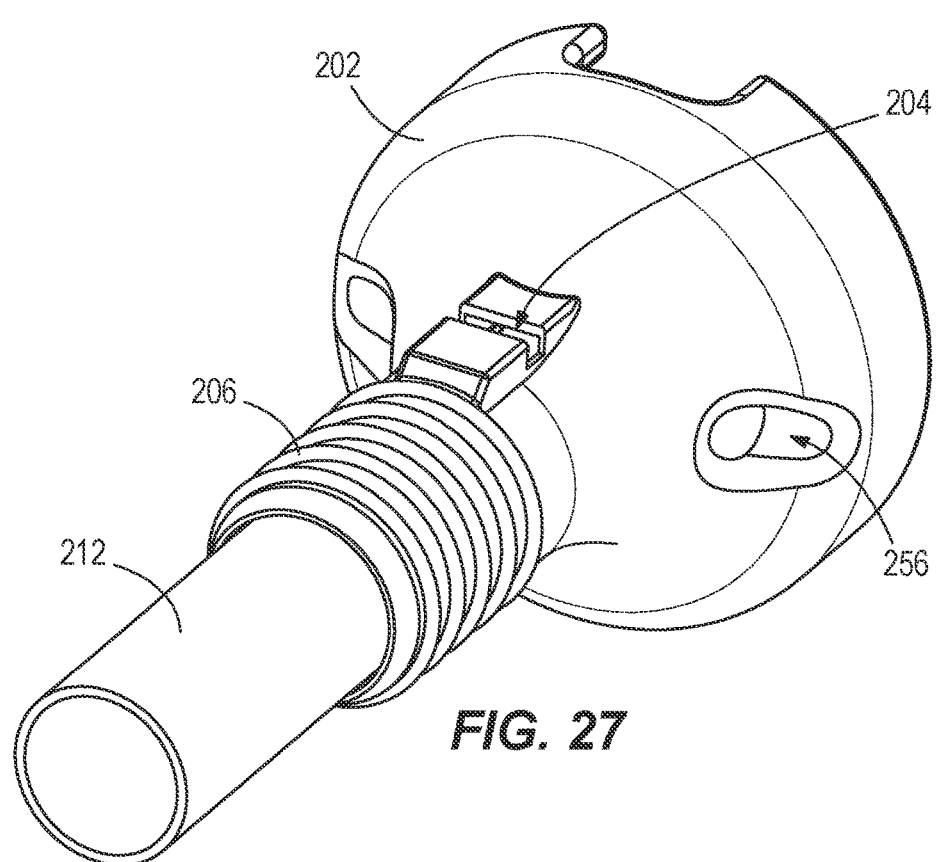
FIG. 27 illustrates a front perspective view of the tube and sleeve of the device of FIG. 19.
Figure 28:
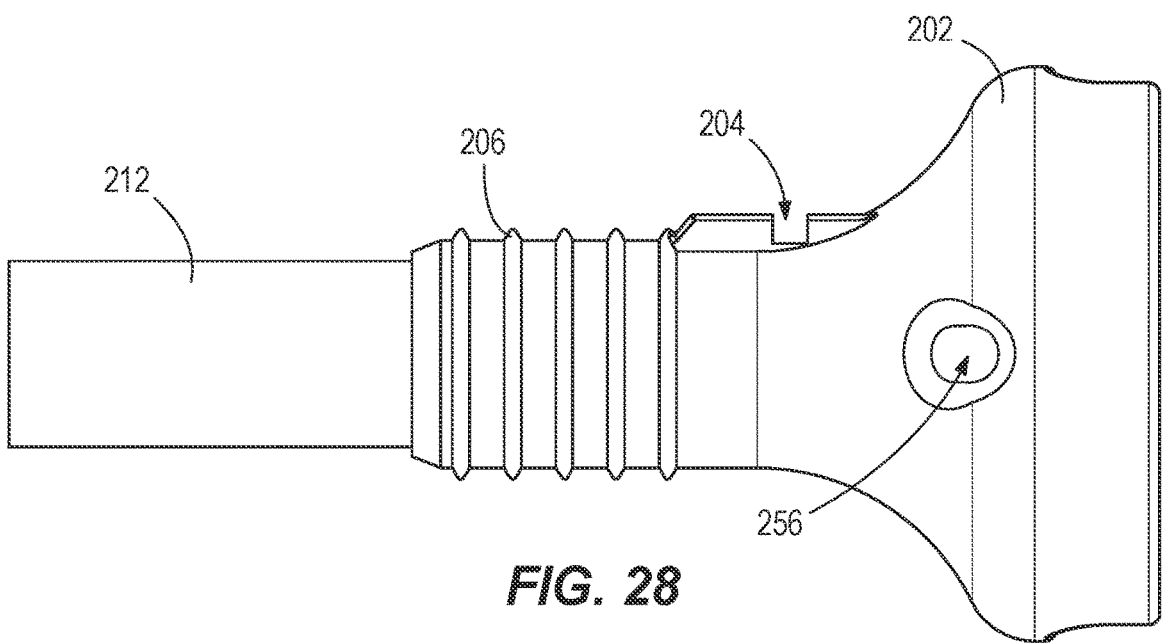
FIG. 28 illustrates a side elevation view of the tube and sleeve of FIG. 27.
Figure 29:
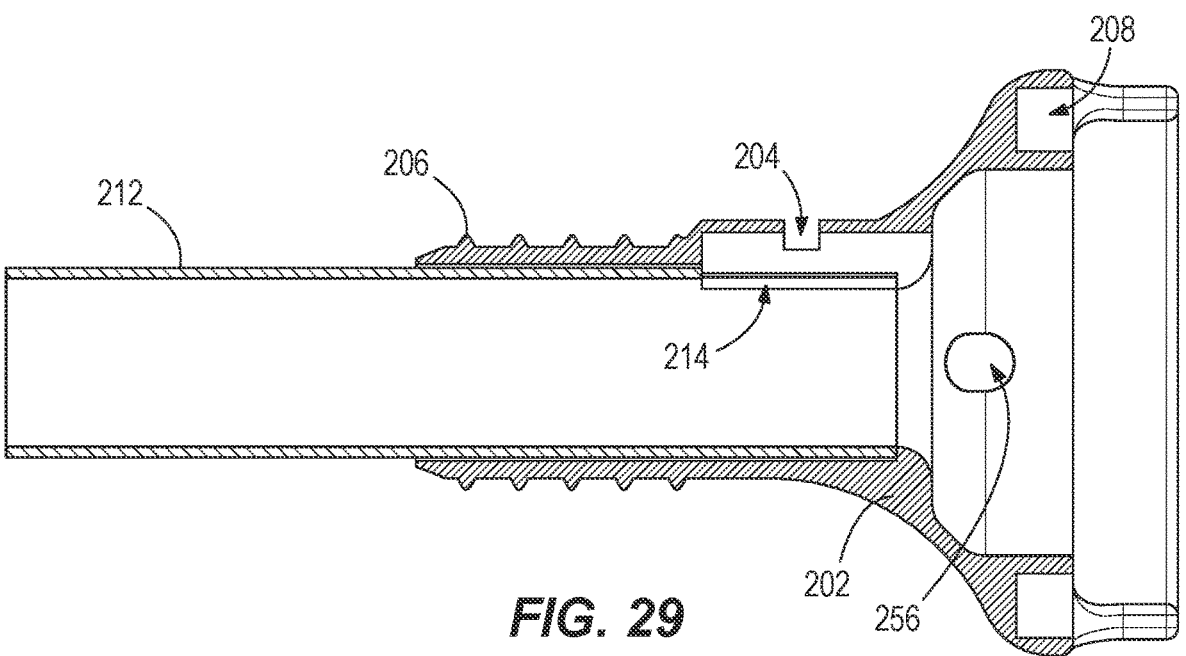
FIG. 29 illustrates a cross-sectional side elevation view of the tube and sleeve of FIG. 27.
Figure 30:
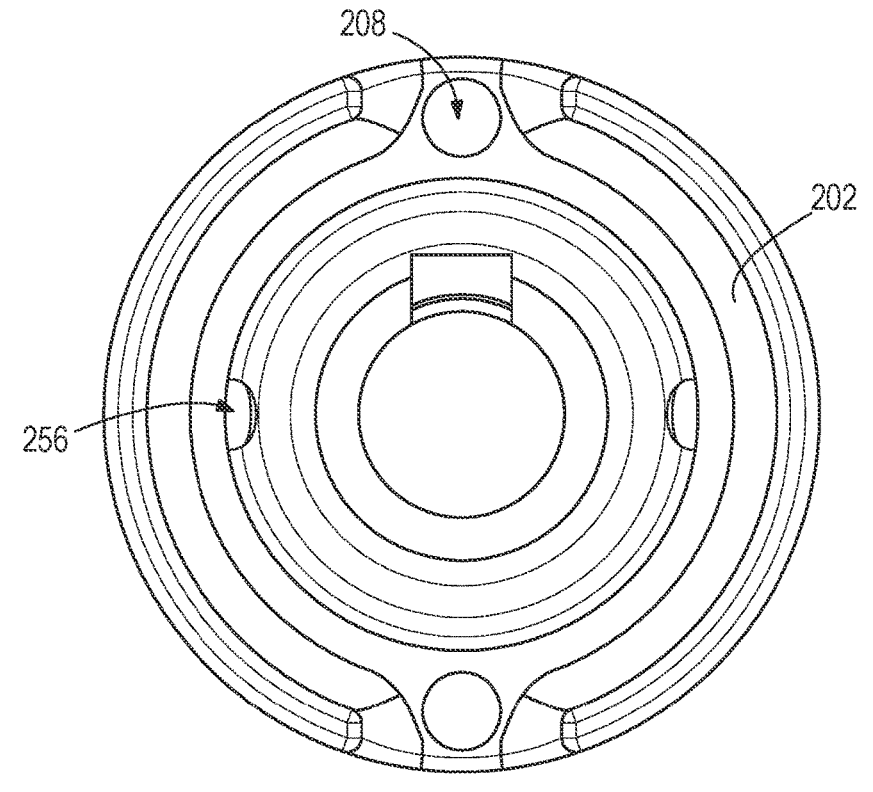
FIG. 30 illustrates a rear elevation view of the tube and sleeve of FIG. 27.
Figure 31:
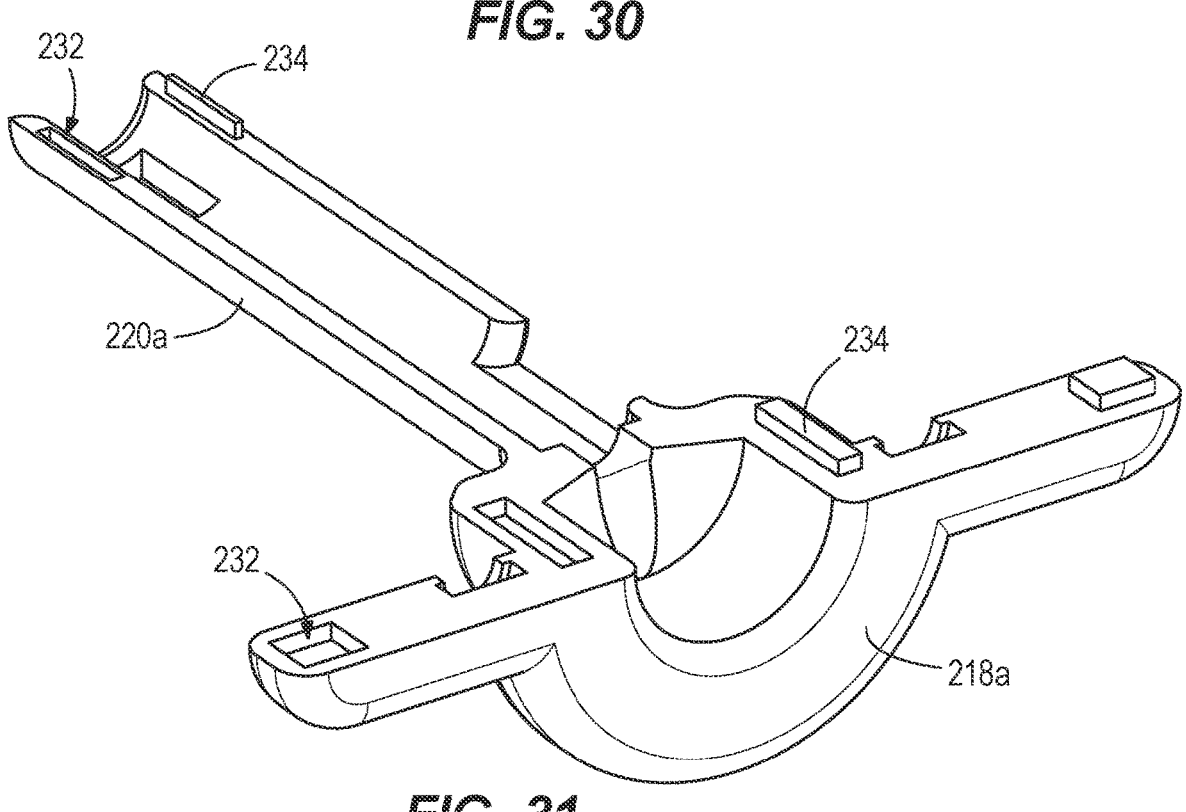
FIG. 31 illustrates a rear perspective view of one half of a handle and sheath of the device of FIG. 19.

As shown in FIG. 26, in the illustrated embodiment, the trocar further includes a light shield 270 disposed in the tip member 222 between the photoresistor 266 and the utility light source 268. The light shield 270 shields the photoresistor 266 from at least some of the light traveling from the utility light source 268 as it passes the photoresistor 266. In this manner, the majority of light detected by the photoresistor 266 is light that has come from the utility light source 268 after it has reflected off of a structure inside the thoracic cavity of a patient back at the photoresistor 266. In the illustrated embodiment, the light shield 270 is shaped like a cup, allowing only the side of the photoresistor 266 facing the distal end of the pointed tip 248 to be unobstructed by the light shield 270. The light shield 270 may direct light from the utility light source 268 around the photoresistor 155 (instead of onto the photoresistor) and out the distal end of the tip member 222 through the pointed tip 248. In some embodiments, the light shield 270 may include a reflective material, such as metal.

The above components, such as the indicator light sources 264, the photoresistor 266, the utility light source 268, and the light shield 270 have been described as being placed inside the sheath 220 and/or handle 218. In some embodiments, these components are removably disposed inside the sheath 220 and/or handle 218, but other embodiments may include these components permanently fixed in place. In some embodiments, adhesive or some other fastener may be utilized to permanently fix the components in place. In still other embodiments, these electrical components may be insert molded into the polymer sheath 220 and/or handle 218.

The device 200, therefore, includes indicator light sources 264 that may dim or even turn off during moments when the photoresistor 266 receives light reflected off of, for instance, the patient's liver, spleen, intestines, or other internal structure. The indicator light sources 264 may shine brightly when the pointed tip 248 is located properly in the thoracic cavity (e.g., sufficiently far from any internal structures that a relatively low amount of light is reflected back onto the photoresistor 266). Accordingly, a user may be confident that the device 200 is properly placed upon bright illumination of the indicator light sources 264.

The following embodiment of the device 300 shares many similarities with the embodiment of the device 100 described above. In the interest of brevity, not all components of the device 300 below will be described. Rather, only differences between the embodiments and/or further details not explored above will be described. Like components will be numbered the same as the corresponding components of the device 100 but increased by a value of two hundred.

Figure 36:
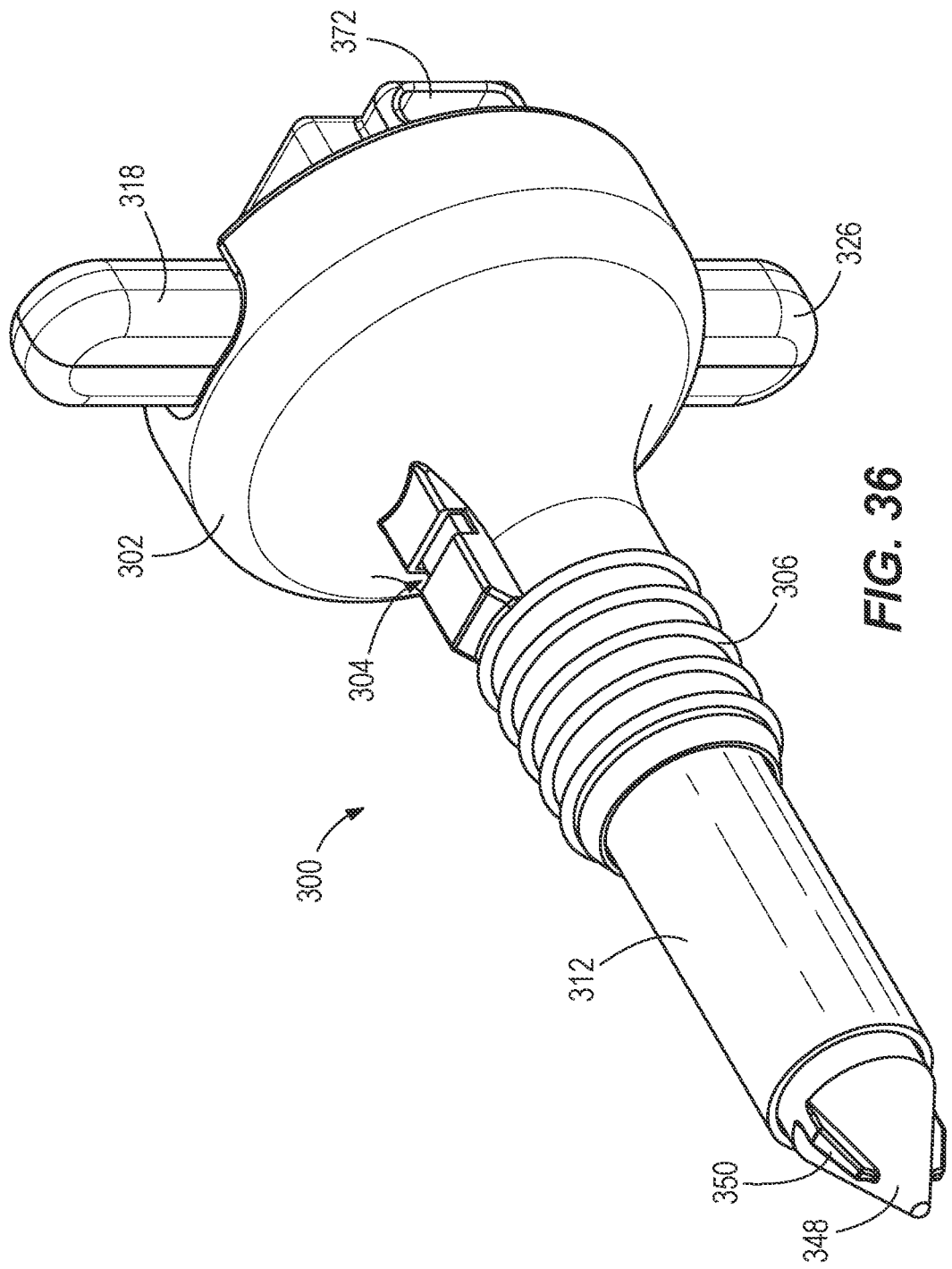
FIG. 36 illustrates a front perspective view of a device for accessing a cavity in a subject, according to embodiments disclosed herein.
Figure 37:
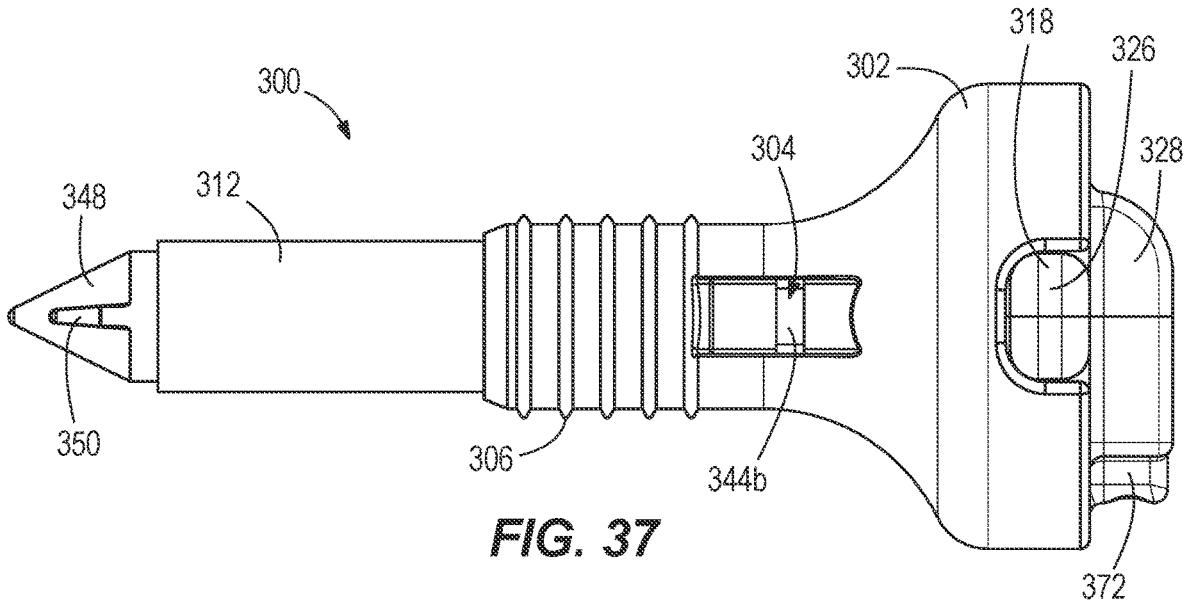
FIG. 37 illustrates a top plan view of the device of FIG. 36.
Figure 38:
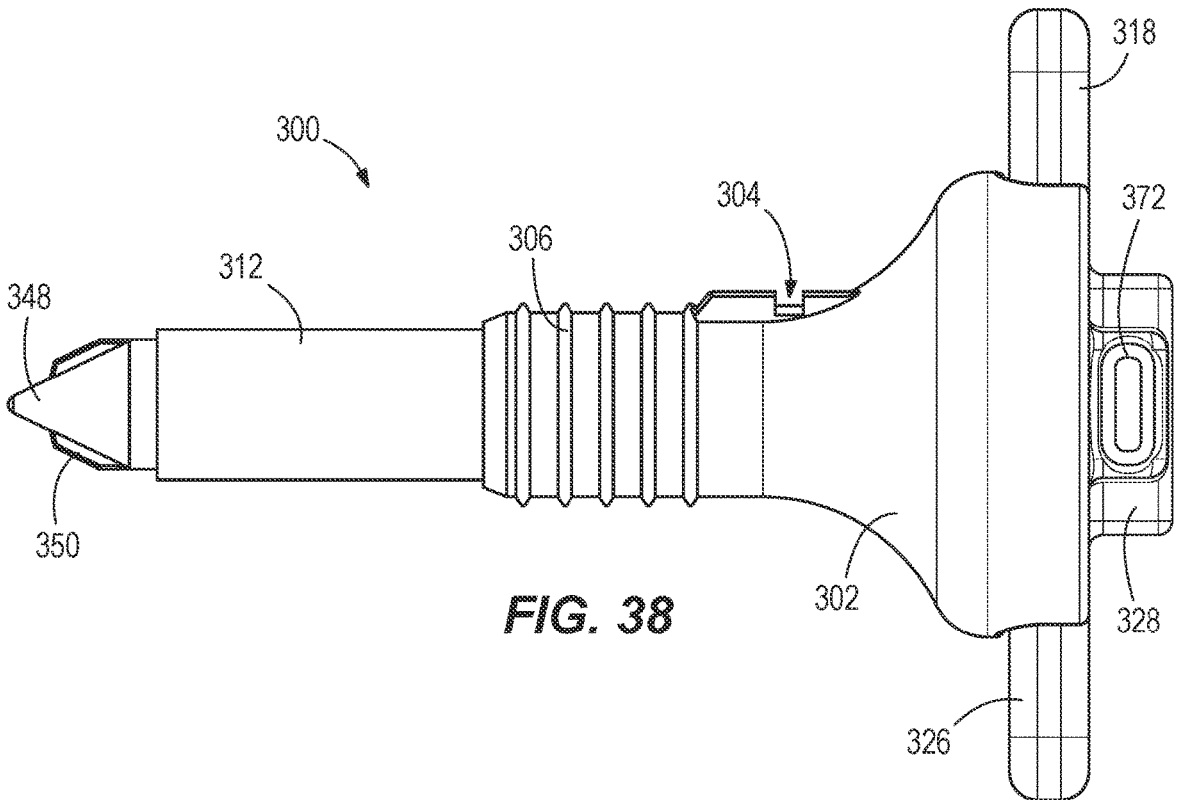
FIG. 38 illustrates a side elevation view of the device of FIG. 36.
Figure 39:
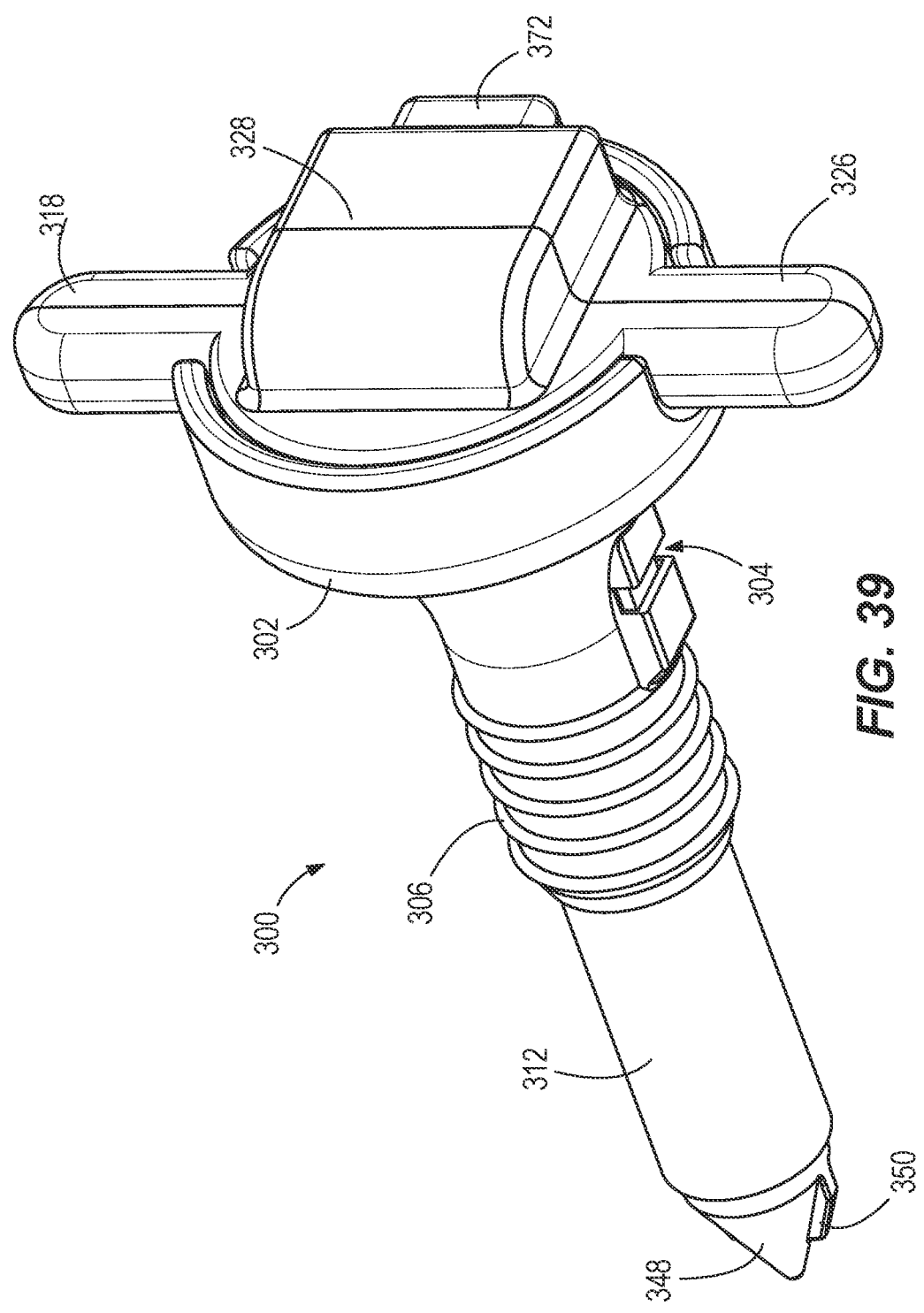
FIG. 39 illustrates a rear perspective view of the device of FIG. 36.

With reference to FIG. 36, yet another embodiment of the device 300 is shown. In this embodiment, the handle 318 includes an electronic port 372 disposed therein. The electronic port 372 may be, for instance, a USB-C port or other appropriate port for connecting a wire, a flash drive, or the like to the device 300. In some embodiments, the device 300 is configured only to send data out via the port 372, but other embodiments may include the device 300 configured to receive data in via the port 372, for instance, to update or adjust the functionality of the device 300. In still other embodiments, the device 300 is configured to be powered only upon connection of a wire to the port 372. Some embodiments, however, may include an internal power source (similar to that disclosed above with regard to the device 200) that is able to power the device 300 even when nothing is connected to the port 372.

Figure 40:
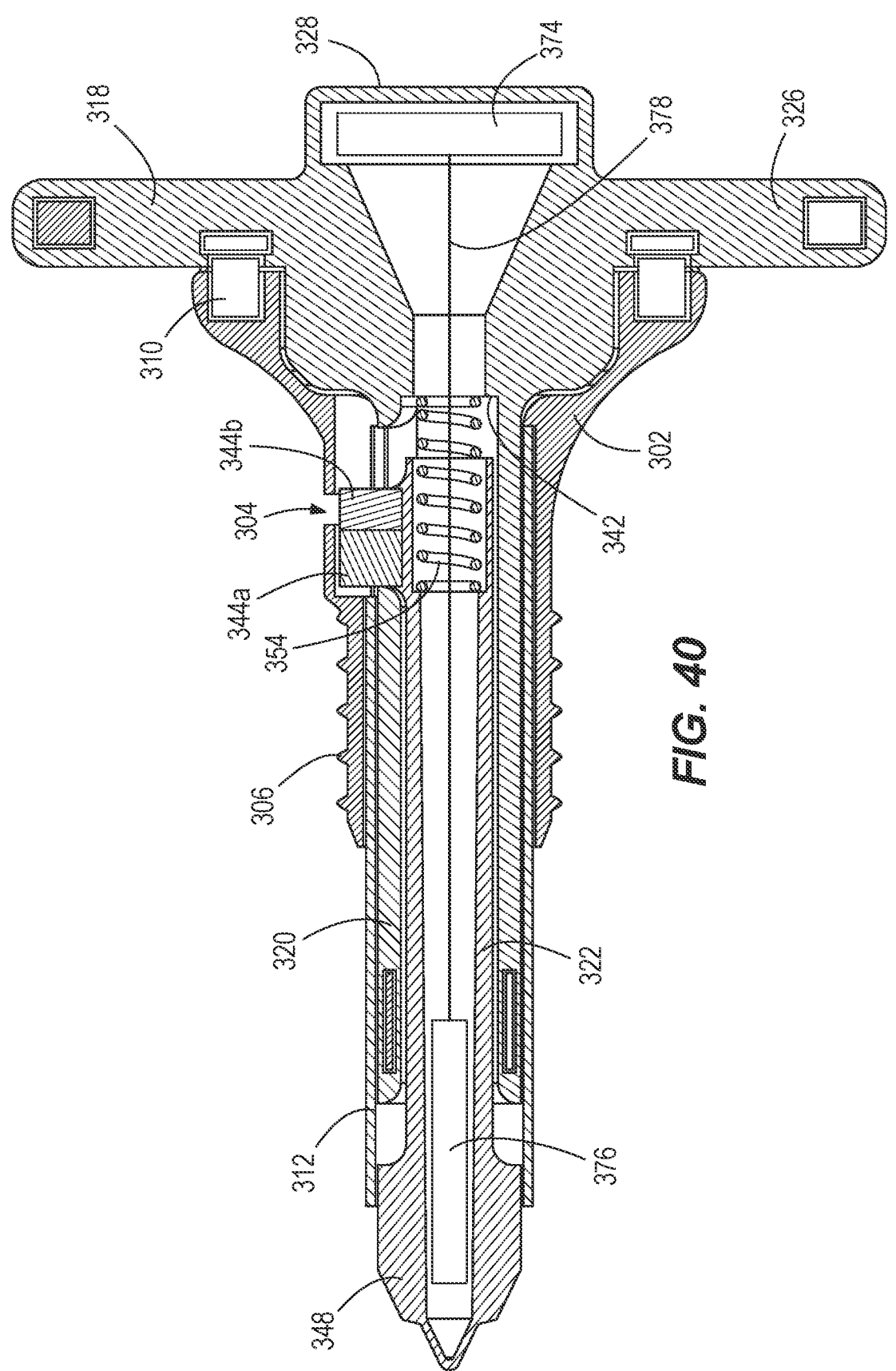
FIG. 40 illustrates a cross-sectional side elevation view of the device of FIG. 36.
Figure 41:
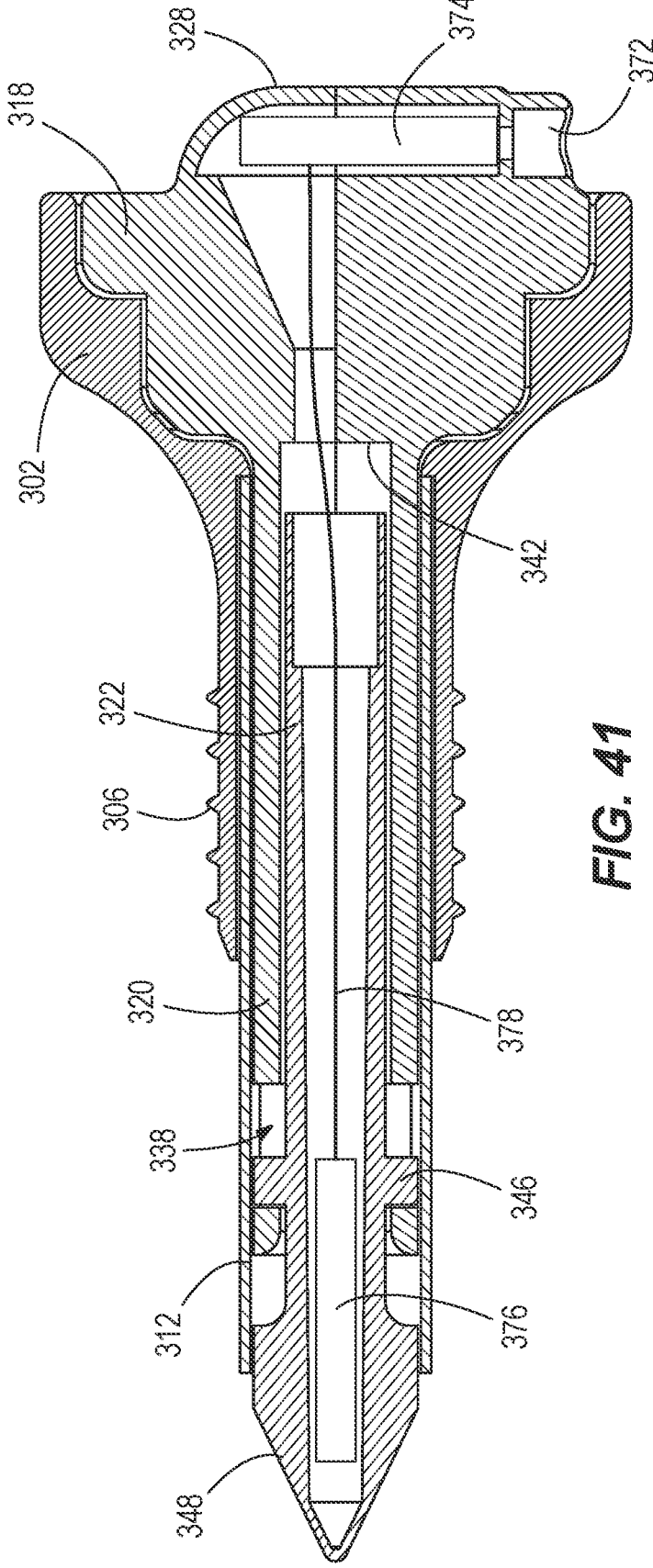
FIG. 41 illustrates a cross-sectional top plan view of the device of FIG. 36.
Figure 42:
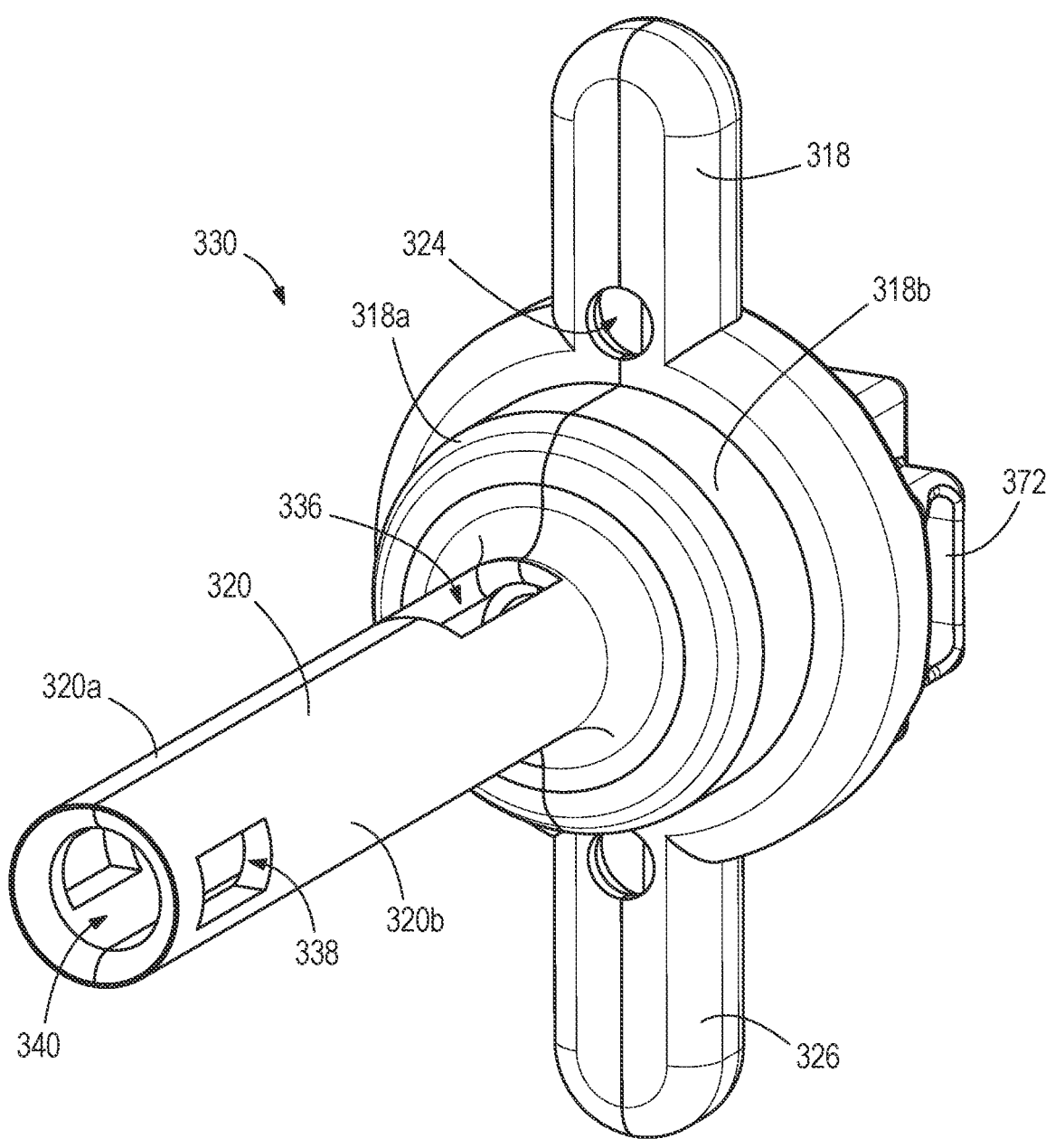
FIG. 42 illustrates a front perspective view of a handle and sheath of the device of FIG. 36.
Figures 43, 44:
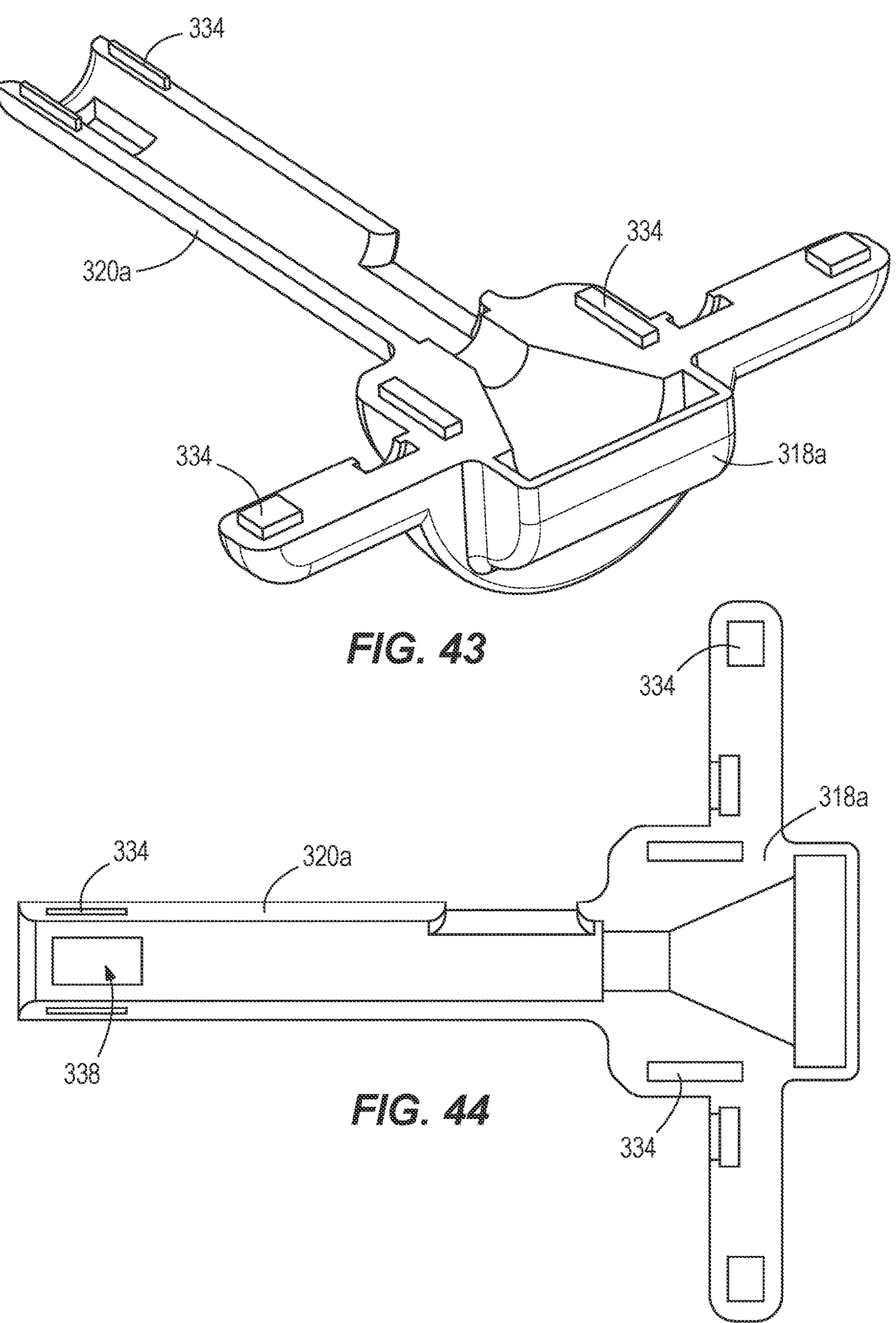
FIG. 43 illustrates a rear perspective view of one half of the handle and sheath of FIG. 42.
FIG. 44 illustrates a side elevation view of the one half of the handle and sheath of FIG. 42.

Turning to FIG. 40, the illustrated embodiment further includes a circuit board 374 disposed in the handle 318 and electrically coupled to the port 372. In some embodiments, the circuit board 374 simply routes power as appropriate. In other embodiments, however, at least some data processing is capable of being achieved with the circuit board 374 such that, for instance, the circuit board 374 may include a processor or controller.

The device 300 further includes a camera 376 disposed in the tip member 322. In the illustrated embodiment, the camera 376 is located adjacent to the pointed tip 348 of the tip member 322. In some embodiments, the camera 376 can be said to be located nearer to the distal end of the tip member 322 than to the handle 318. The camera 376 is arranged such that its viewing field is the area outside of and in front of the pointed tip 348. Stated another way, the camera 376 is directed toward the distal end of the tip member 322. At least a portion of the pointed tip 348 may be transparent. In some embodiments, the entire tip member 322 is transparent. The camera 376 is electrically coupled to the circuit board 374 and to the electronic port 372 via, for instance, a wire 378. In the illustrated embodiment, the wire 378 passes through the center of the coils of the spring 354. While not shown in the device 300, the device 300 may further include a utility light source such as the one discussed above with regard to the device 200. In some embodiments, the device 300 is only capable of outputting a live video feed to another device via the electronic port 372. Other embodiments, however, may include the device 300 capable of storing video data on, for instance, a memory of the circuit board 374.

While not illustrated, other embodiments may include further features, such as a piezoelectric sensor configured to generate an electric signal based on forces experienced by the pointed tip and/or the tip member, a speaker configured to generate an audible signal upon detection of an acceptable placement of the device (according to any method described above), or the like.

Figure 45:
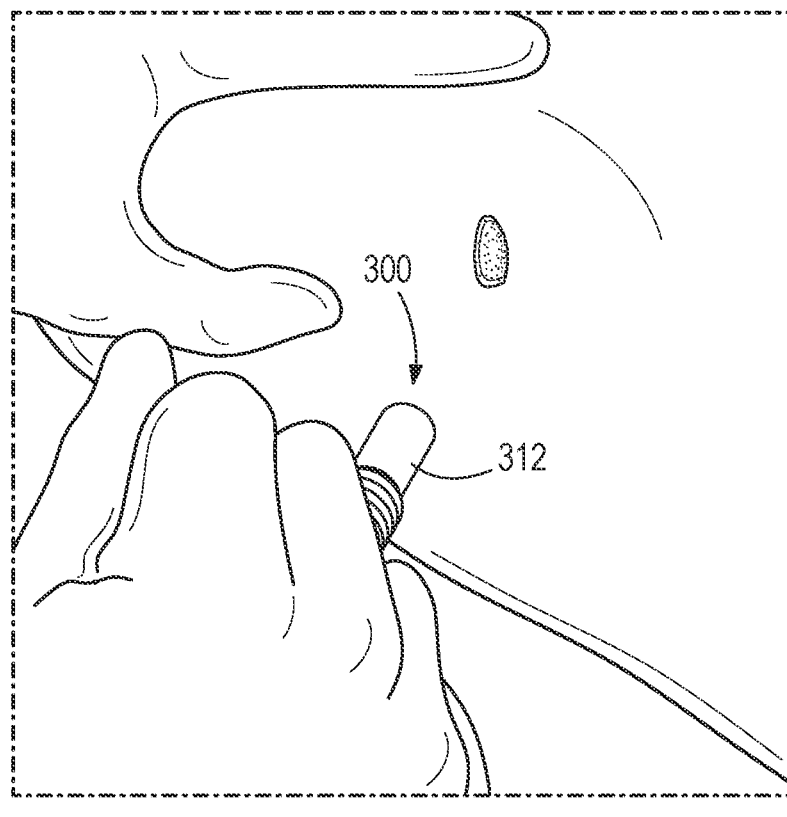
FIG. 45 illustrates a phase of a method of using a device for accessing a cavity in a subject, according to embodiments disclosed herein.
Figure 46:
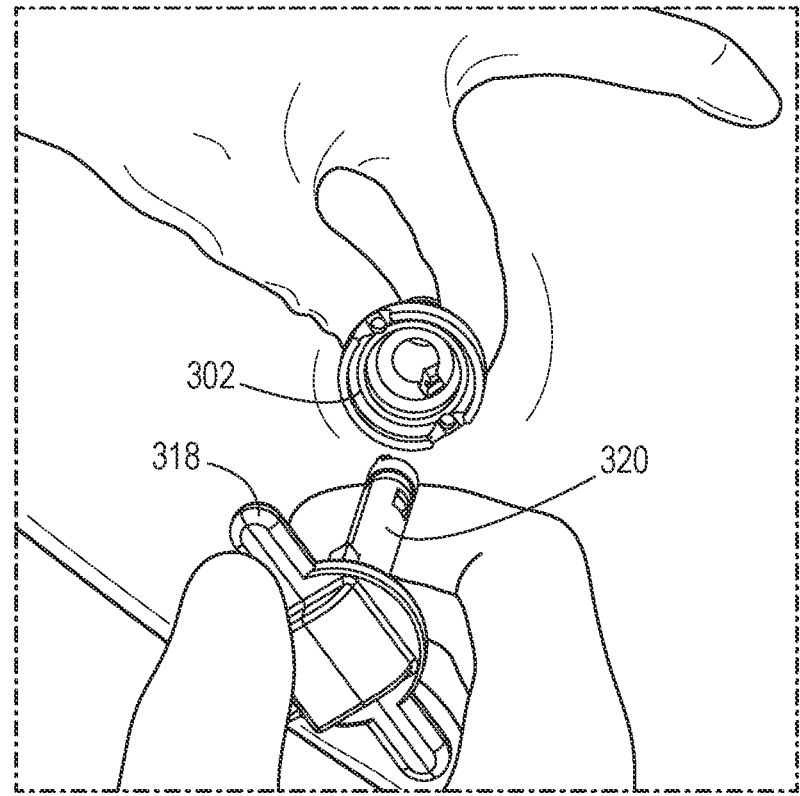
FIG. 46 illustrates another phase of the method.
Figure 47:
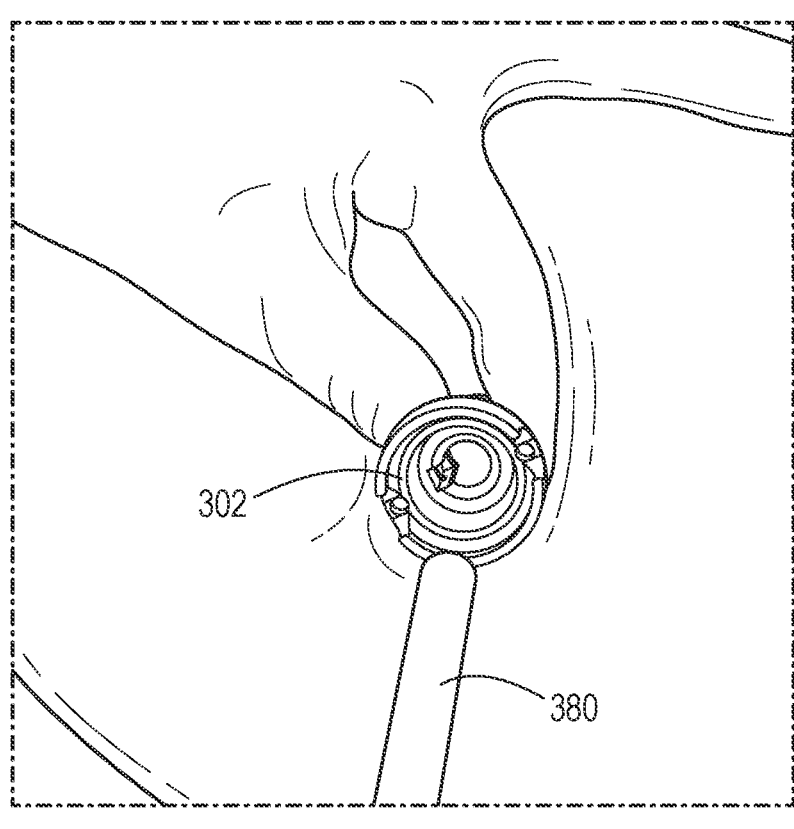
FIG. 47 illustrates yet another phase of the method.
Figure 48:
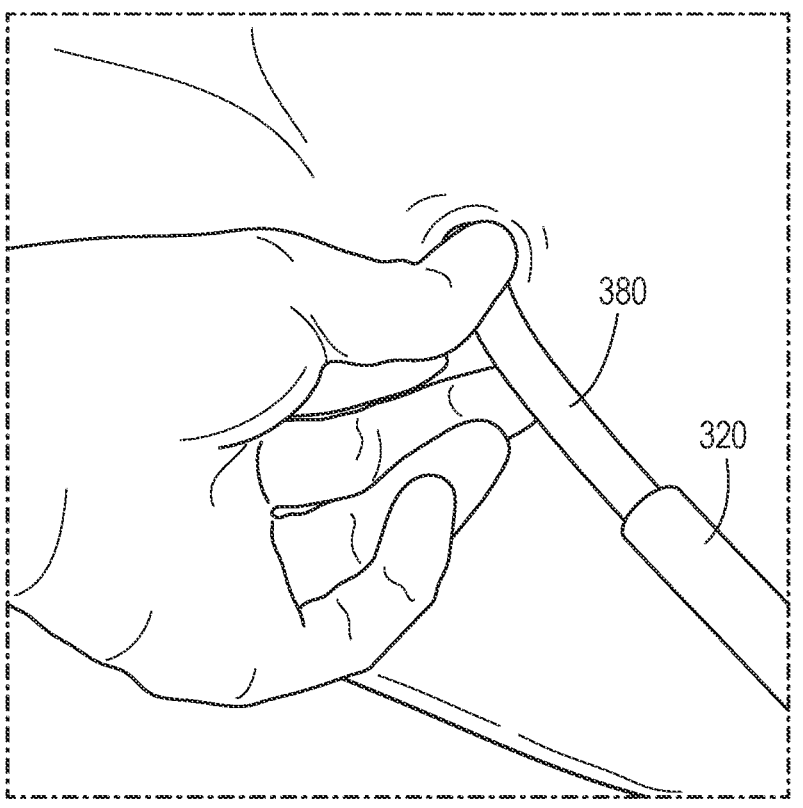
FIG. 48 illustrates still another phase of the method.

With reference to FIGS. 45-48, a method of using the device 300 that includes a utility light source is shown. The device 300 is used on a non-human animal in these figures (a porcine model). FIG. 45 shows the incision that has been made in the chest between adjacent ribs. The device 300 is illuminating the incision with the utility light source. FIG. 46 shows the device 300 inserted into the incision and the user pulling the trocar (handle 318 and sheath 320) out of the tube 312 and sleeve 302. FIG. 47 shows the tube 312 and the sleeve 302 positioned to accept a cannula 380 that is ready to be inserted into the thoracic cavity. FIG. 48 shows the cannula 380 positioned in the thoracic cavity through the tube 312 and sleeve 302 while the user is removing the tube 312 and sleeve 302 by pulling the tube 312 and sleeve 302 over the remainder of the cannula 380 that is outside of the thoracic cavity.

While not described in detail, the present disclosure contemplates the use of the same or similar embodiments of the device described above for other procedures, such as a tracheotomy.

Various features and advantages of some embodiments are set forth in the following claims.

What is claimed is:

1. A device for accessing a cavity, the device comprising:
a tube;
a trocar extending through the tube, the trocar including
a handle,
a sheath opposite the handle, and
a tip member disposed in the sheath and biased in an extension direction away from the handle, at least a portion of the tip member extending beyond the sheath in the extension direction throughout operation of the device, the tip member including an indicator indicating a position of the tip member relative to the handle.

2. The device of claim 1, further comprising a coil spring disposed between the tip member and the handle, the spring biasing the tip member in the extension direction.

3. The device of claim 1, wherein the indicator includes an extended section and a retracted section, the extended section having a different appearance than the retracted section.

4. The device of claim 3, wherein the extended section is a different color than the retracted section.

5. The device of claim 1, wherein
the sheath includes an opening defined therein, and
the indicator of the tip member extends through the opening.

6. The device of claim 5, wherein
the tube includes a notch defined therein, and
the indicator of the tip member extends through the notch.

7. The device of claim 1, wherein
the sheath includes a wall having a radially open channel defined in the wall of the sheath, and
the tip member includes a radially extending protrusion slidably disposed in the channel.

8. The device of claim 1, further comprising a sleeve disposed around the trocar, the sleeve including a slot defined therein, the indicator of the tip member disposed inside the sleeve and aligned with the slot.

9. The device of claim 1, wherein a longitudinal half of each of the handle and the sheath are formed together as a unitary part.

10. A device for accessing a cavity, the device comprising:
a tube; and
a trocar extending through the tube, the trocar including
a handle, a power source disposed in the handle,
an indicator light source disposed in the handle, the indicator light source electrically coupled to the power source and configured to project light outside of the handle,
a sheath opposite the handle, the sheath including an interior passage,
a tip member disposed in the sheath and movable from an extended position to a retracted position, the tip member biased in an extension direction away from the handle toward the extended position, the tip member including a distal end opposite the handle extending beyond the sheath in the extension direction in both the extended position and the retracted position, the distal end of the tip member being wider than the interior passage of the sheath,
a photoresistor disposed in the tip member nearer to the distal end of the tip member than to the handle, the photoresistor electrically coupled to the power source and to the indicator light,
a utility light source disposed in the tip member between the handle and the photoresistor, the utility light source electrically coupled to the power source, and
a light shield disposed between the photoresistor and the utility light source to direct light from the utility light source around the photoresistor and out the distal end of the tip member.

11. The device of claim 10, wherein
the tip member is translucent, and
light from the utility light source passes through the tip member.

12. The device of claim 10, wherein the light shield surrounds all sides of the photoresistor other than a side of the photoresistor facing the distal end of the tip member.

13. The device of claim 10, wherein
at least a portion of the handle of the trocar is translucent, and
light from the indicator light source passes through the handle.

14. The device of claim 10, further comprising a sleeve disposed around the trocar, the sleeve including an opening defined therein, and wherein light from the indicator light source passes through the opening.

15. The device of claim 14, wherein the trocar is removably coupled to the sleeve.

16. The device of claim 10, wherein the handle includes a removable cap to allow access to the power source.

17. A device for accessing a cavity, the device comprising:
a tube; and
a trocar extending through the tube, the trocar including
a handle,
a sheath opposite the handle, the sheath including an interior passage,
a tip member disposed in the sheath and movable from an extended position to a retracted position, the tip member biased in an extension direction away from the handle toward the extended position, the tip member including a distal end opposite the handle extending beyond the sheath in the extension direction in both the extended position and the retracted position, at least a portion of the tip member being wider than the interior passage of the sheath, the portion of the tip member being nearer to the distal end than to the handle, a camera disposed in the tip member nearer to the distal end of the tip member than to the handle, the camera directed toward the distal end of the tip member; and an electronic port disposed in the handle, the electronic port electrically coupled to the camera.

18. The device of claim 17, wherein the tip member is transparent.

19. The device of claim 17, further comprising a circuit board disposed in the handle, and wherein the electronic port is disposed on the circuit board.

20. The device of claim 17, wherein the electronic port includes a USB-C port.

* * * * *